(12) United States Patent
Steusloff et al.

(10) Patent No.: US 7,607,571 B2
(45) Date of Patent: Oct. 27, 2009

(54) MEDICAL WORK FLOW SYSTEM

(75) Inventors: Patrick M. Steusloff, San Diego, CA (US); David D. Swenson, Encinitas, CA (US)

(73) Assignee: IntelliDOT Corporation, San Diego, CA (US)

( * ) Notice: Subject to any disclaimer, the term of this patent is extended or adjusted under 35 U.S.C. 154(b) by 941 days.

(21) Appl. No.: 10/857,701

(22) Filed: May 28, 2004

(65) Prior Publication Data

US 2004/0243444 A1 Dec. 2, 2004

Related U.S. Application Data

(60) Provisional application No. 60/475,173, filed on May 30, 2003, provisional application No. 60/530,073, filed on Dec. 16, 2003, provisional application No. 60/560,084, filed on Apr. 7, 2004.

(51) Int. Cl.
*G06K 7/10* (2006.01)
(52) U.S. Cl. .......................... 235/375; 235/382; 705/2; 705/3
(58) Field of Classification Search .................. 235/375, 235/382; 705/2, 3
See application file for complete search history.

(56) References Cited

U.S. PATENT DOCUMENTS

| | | |
|---|---|---|
| 4,761,544 A | 8/1988 | Poland |
| 4,825,058 A | 4/1989 | Poland |
| 4,835,372 A | 5/1989 | Gombrich et al. |
| 4,857,713 A | 8/1989 | Brown |
| 4,857,716 A | 8/1989 | Gombrich et al. |
| 4,868,375 A | 9/1989 | Blanford |
| 4,916,441 A | 4/1990 | Gombrich |
| 5,185,514 A | 2/1993 | Wike et al. |
| 5,272,318 A | 12/1993 | Gorman |
| 5,296,688 A | 3/1994 | Hamilton et al. |
| 5,315,505 A | 5/1994 | Pratt et al. |
| 5,444,779 A | 8/1995 | Daniele |
| 5,592,374 A | 1/1997 | Fellegara et al. |
| 5,640,193 A | 6/1997 | Wellner |
| 5,805,779 A | 9/1998 | Christopher et al. |
| 5,822,544 A | 10/1998 | Chaco et al. |

(Continued)

FOREIGN PATENT DOCUMENTS

EP 1001605 A2 5/2000

(Continued)

OTHER PUBLICATIONS

Partial European Search Report EP 04012826 dated Apr. 4, 2007.

*Primary Examiner*—Allyson N Trail
(74) *Attorney, Agent, or Firm*—Knobbe, Martens, Olson & Bear LLP

(57) ABSTRACT

A system is described for managing data and information in a healthcare environment, such as a hospital. A handheld code scanner reads codes and either accepts data, or performs instructions based on the read code. The code scanner wirelessly transmits the codes or data to a central server which acts on the read code to carry out necessary functions. The system is useful for tracking patient data, such as for delivery of medicine. In addition, since the system can carry out instructions, it is useful for allowing healthcare workers to quickly and conveniently perform their duties without the necessity of sitting at a computer terminal.

33 Claims, 17 Drawing Sheets

U.S. PATENT DOCUMENTS

| | | | |
|---|---|---|---|
| 5,841,978 A | 11/1998 | Rhoads | |
| 5,844,227 A | 12/1998 | Schmidt et al. | |
| 5,845,264 A | 12/1998 | Nellhaus | |
| 5,869,819 A | 2/1999 | Knowles et al. | |
| 5,905,248 A | 5/1999 | Russell et al. | |
| 5,932,863 A | 8/1999 | Rathus et al. | |
| 5,933,811 A | 8/1999 | Angels et al. | |
| 5,979,757 A | 11/1999 | Tracy et al. | |
| 6,045,048 A | 4/2000 | Wilz, Sr. et al. | |
| 6,076,733 A | 6/2000 | Wilz, Sr. et al. | |
| 6,082,776 A | 7/2000 | Feinberg | |
| 6,325,283 B1 | 12/2001 | Chu et al. | |
| 6,415,295 B1 | 7/2002 | Feinberg | |
| 6,464,136 B2 | 10/2002 | Walsh | |
| 6,542,902 B2 | 4/2003 | Dulong et al. | |
| 6,601,772 B1 | 8/2003 | Rubin et al. | |
| 6,757,850 B1 | 6/2004 | Lehner | |
| 6,827,273 B2 | 12/2004 | Wilz et al. | |
| 2001/0035459 A1* | 11/2001 | Komai | 235/462.25 |
| 2002/0038298 A1 | 3/2002 | Kusakabe et al. | |
| 2002/0045355 A1 | 4/2002 | Chong et al. | |
| 2002/0095238 A1 | 7/2002 | Ahlin et al. | |
| 2002/0099274 A1 | 7/2002 | Isomura et al. | |
| 2002/0147390 A1 | 10/2002 | Markis et al. | |
| 2002/0169636 A1 | 11/2002 | Eggers et al. | |
| 2002/0188472 A1 | 12/2002 | Fujisaka et al. | |
| 2002/0195488 A1 | 12/2002 | Walsh | |
| 2003/0052787 A1 | 3/2003 | Zerhusen et al. | |
| 2003/0055685 A1 | 3/2003 | Cobb et al. | |
| 2003/0195774 A1 | 10/2003 | Abbo | |
| 2004/0039607 A1* | 2/2004 | Savitz et al. | 705/3 |
| 2004/0210515 A1* | 10/2004 | Hughes | 705/39 |
| 2004/0232219 A1* | 11/2004 | Fowler | 235/380 |
| 2004/0262395 A1 | 12/2004 | Longacre et al. | |
| 2004/0262399 A1 | 12/2004 | Longacre et al. | |
| 2005/0103852 A1 | 5/2005 | Lucera et al. | |

FOREIGN PATENT DOCUMENTS

| | | |
|---|---|---|
| GB | 2327565 A | 1/1999 |
| WO | WO 99/10830 | 3/1999 |
| WO | WO 99/17230 | 4/1999 |
| WO | WO 00/28455 | 5/2000 |
| WO | WO 01/86574 | 11/2001 |
| WO | WO 02/07065 A2 | 1/2002 |
| WO | WO 02/21794 A2 | 3/2002 |
| WO | WO 03/060805 | 7/2003 |

* cited by examiner

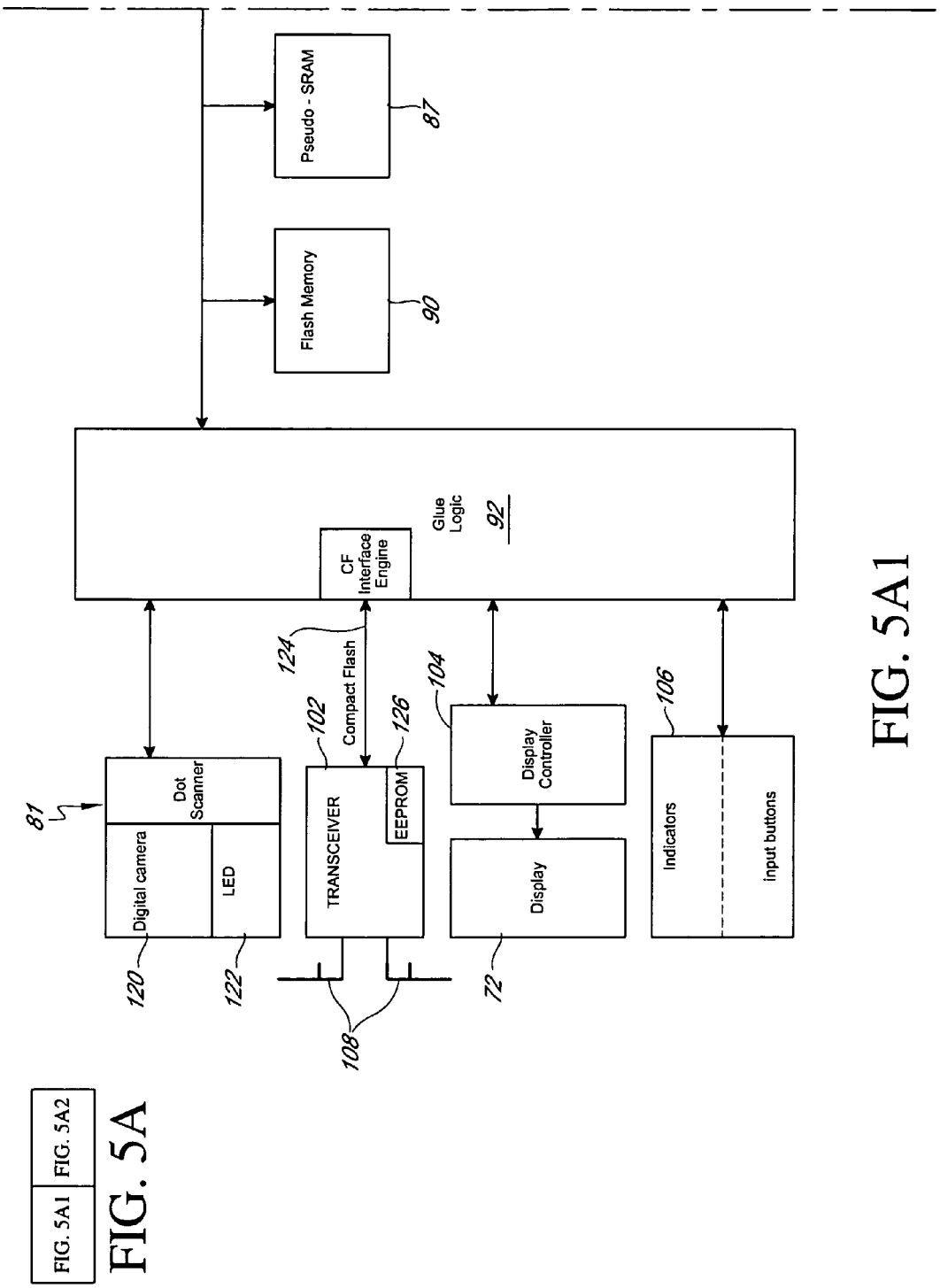

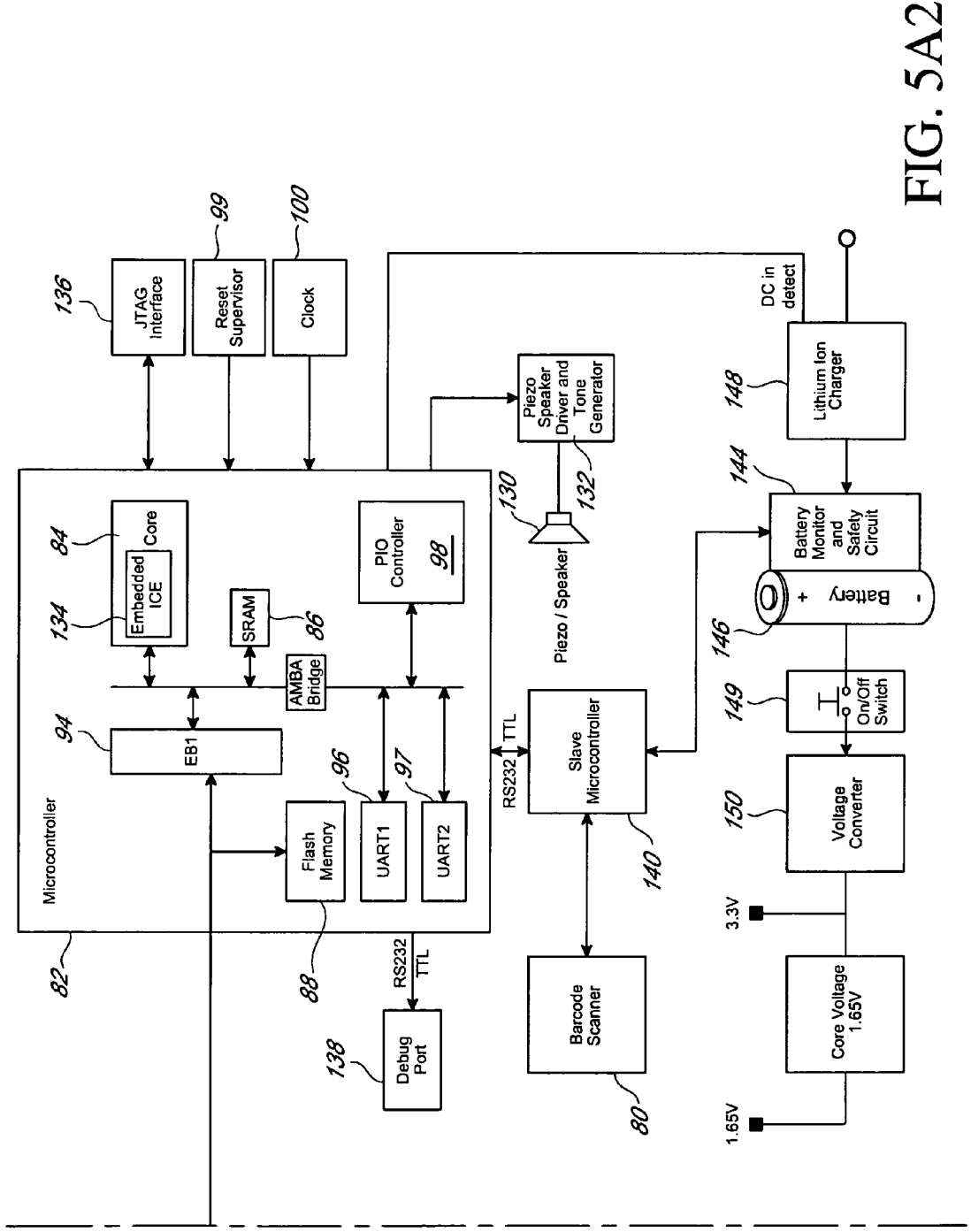
FIG. 5A2

Medication Worksheet

ABC Medical Center
Nurse: Forth, Gerry
Report Date: 12/6/03
Shift: 07:00-19:00

| | 8 | 10 | 12 | 14 | 16 | 18 | NOTES |
|---|---|---|---|---|---|---|---|
| Baker, Dave 333 1 | | | | | | | |
| DOCUSATE SODIUM 100MG PO BID | | | | | | | |
| DIGOXIN 0.25MG PO QD | | | | | | | |
| FUROSEMIDE 20MG PO QD | | | | | | | |
| MEPERIDINE HCL INJ 50-75MG IM PRN | | | | | | | |
| Payne, Gerry 334 1 | | | | | | | |
| DOCUSATE SODIUM 100MG PO BID | | | | | | | |
| DIGOXIN 0.25MG PO QD | | | | | | | |
| FUROSEMIDE 20MG PO QD | | | | | | | |
| MEPERIDINE HCL INJ 50-75MG IM PRN | | | | | | | |
| Baker, Dave 333 1 | | | | | | | |
| DOCUSATE SODIUM 100MG PO BID | | | | | | | |
| DIGOXIN 0.25MG PO QD | | | | | | | |
| FUROSEMIDE 20MG PO QD | | | | | | | |
| MEPERIDINE HCL INJ 50-75MG IM PRN | | | | | | | |
| Smith, Patrick 336 1 | | | | | | | |
| DOCUSATE SODIUM 100MG PO BID | | | | | | | |
| DIGOXIN 0.25MG PO QD | | | | | | | |
| FUROSEMIDE 20MG PO QD | | | | | | | |
| MEPERIDINE HCL INJ 50-75MG IM PRN | | | | | | | |

| Sites | | | Override Reasons | |
|---|---|---|---|---|
| R. THIGH | L. THIGH | L. LOWER ABD. | Start Order | New Order |
| R. LOWER ABD. | R. DELTOID | L. DELTOID | Post-Op | Increased Pain |
| BOTH EYES | BOTH EARS | L. UPPER ABD | Increased Nausea | VS Warranted |
| R. UPPER ABD. | | | Pt.Cond.Warrants | Standing Order |
| | | | New Route | New Schedule |

| Keypad | | | Other | | | |
|---|---|---|---|---|---|---|
| 1 | 2 | 3 | Cancel All | Continue | Omit | Logout |
| 4 | 5 | 6 | Unordered Med Prep Cover Patients | | Tether | Previous |
| 7 | 8 | 9 | | | | |
| * | 0 | # | Next | Enter Later | Gerry Reset Dot | Page S Felner RN |
| Cancel | | back | | | | |

Printed By: Forth, Gerry     Page 1 of 1     Printed At: 12/06/2003 12:38

FIG. 12

MEDICAL WORK FLOW SYSTEM

CROSS REFERENCE TO RELATED APPLICATION

This application claims priority to U.S. Provisional Patent Application 60/475,173 entitled "MEDICAL MANAGEMENT SYSTEM" and filed on May 30, 2003, U.S. Provisional Patent Application 60/530,073 entitled "MEDICAL WORK FLOW SYSTEM" and filed on Dec. 16, 2003, and U.S. Provisional Patent Application 60/560,084 entitled "MEDICAL WORK FLOW SYSTEM" and filed on Apr. 7, 2004. The disclosures of the above-described filed applications are hereby incorporated by reference in their entirety.

BACKGROUND OF THE INVENTION

1. Field of the Invention

The present invention relates generally to a system for controlling data in a health care environment. More particularly, the present invention relates to a medical processing system that includes a handheld scanner that uses a code scanner for entering commands and data into a medical management system.

2. Description of the Related Art

Some computing tasks or environments require a high degree of mobility, ease of operation, and low cost implementation due to a large number of users. One example of such tasks is the administration and documentation of care provided to patients in a medical or hospital environment. Computer resources in these environments are limited due to inadequate availability of access points such as input/output (I/O) stations or terminals. Although stationary terminals have a large screen, familiar full-featured keyboard, and mouse input devices, such terminals are inconvenient to use in certain environments due to lack of portability, or availability due to cost and space constraints. Notebook computers with wireless communication capabilities can increase the power of computer terminals while maintaining relatively fast and available computing power. However, they are still somewhat large in size, bulky to transport, have limited battery life, require two hands to operate, and are expensive.

A plurality of small sized wireless computing devices have been developed, such as wireless personal digital assistants (PDA's), for use by caregivers in administration and documentation of medical care. For example, U.S. Pat. No. 4,916,441 to Gombrich describes a handheld terminal that includes a wireless transmitter and a bar code scanner for entering medical data into a computer system. Unfortunately, a nurse needs to manually type much of the information onto a small keyboard on the device. This is inconvenient and time-consuming in a hospital environment.

In addition, similar devices are either fragile or bulky, expensive, and require two-handed or tedious tasks for operation. Thus, improved devices and methods are needed in the technology.

SUMMARY OF THE INVENTION

In one aspect of the invention a system for managing administration of medical care comprises a handheld terminal, comprising a code scanner and a wireless transmitter, wherein the terminal is configured to scan codes corresponding to instructions to be performed by the system, and a computer, configured to receive the codes from the handheld terminal and initiate a process in response to the codes.

In an additional aspect of the invention, the computer is in data communication with at least one peripheral device, and the instructions comprise instructions to be performed by the at least one peripheral device. The peripheral device can be a printer or a messaging system.

In certain embodiments, the terminal is configured to process the instructions. The terminal can further be configured to transmit user information with the codes read by the code reader to the computer. The terminal can also comprise a display for displaying messages to a user, and a button for receiving input from a user.

In another aspect of the invention a wireless terminal for use in medical care administration management system comprises a code scanner, configured to read codes corresponding to information and instructions, and a transceiver, configured to transmit the codes read by the code scanner to a system computer for processing, wherein the system initiates a process in response to a code corresponding to an instruction.

The system can be further configured to execute instructions in response to the scan code reading a code corresponding to an instruction. In one embodiment, the wireless terminal stores user information and transmits the user information with the codes read by the code scanner. In yet another embodiment, the terminal comprises a display for displaying messages to a user. The terminal can also comprise an entry button for receiving input from a user.

Yet another aspect of the invention is a method of controlling processes in a wireless communication system, comprising scanning at least one machine readable code using a wireless terminal, and initiating a process by matching the machine readable code with a corresponding instruction and thereafter performing the instruction.

In one embodiment, the method further comprises transmitting the scanned code via wireless communication to a computer system, wherein the computer system initiates the process. In an additional embodiment, initiating the process comprises sending the instructions to a peripheral system for execution. The method can further comprise analyzing the scanned code to determine whether the code corresponds to data or an instruction.

BRIEF DESCRIPTION OF THE DRAWINGS

The present invention is described with reference to the accompanying drawings. In the drawings, like reference numbers indicate like elements.

FIG. 5A is a block diagram of components within one embodiment of a wireless terminal.

FIG. 12 is an exemplary illustration of one embodiment of a Medication Worksheet for use in a medical management system.

DETAILED DESCRIPTION OF THE PREFERRED EMBODIMENT

Figure 1:
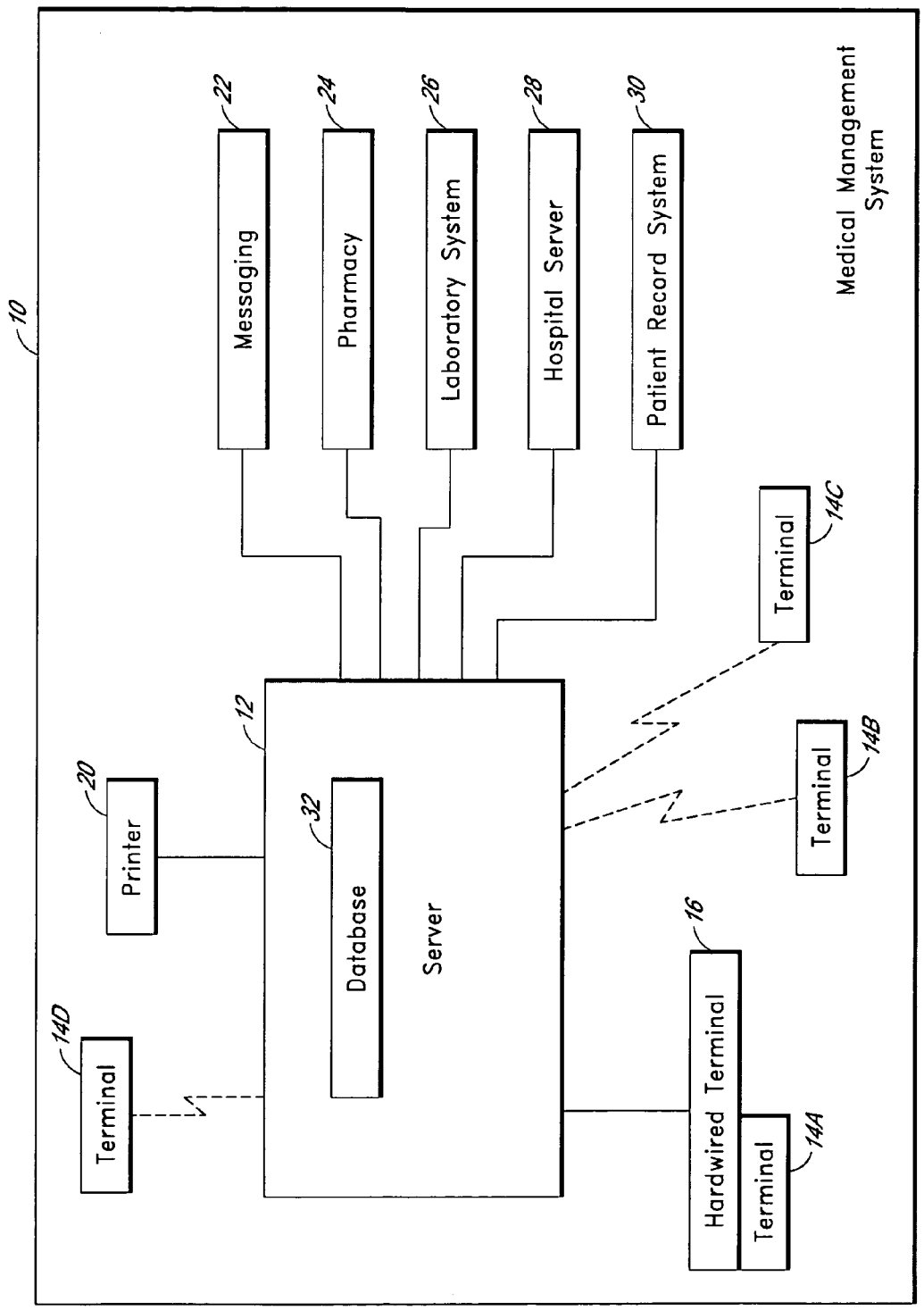
FIG. 1 is a block diagram of one embodiment of a medical management system.

Embodiments of the invention relate to a system and method employing a wireless handheld terminal for management of medical care in an environment such as a hospital. The wireless terminal preferably has at least one code reader, or scanner, used to read codes corresponding to, for example, patient identification, item identification, documentation characters and phrases, commands, and instructions. The codes are preferably machine readable codes, including one and two dimensional optically readable codes such as bar codes, but can include radio frequency identification (RF ID) devices or tags. The codes can be applied to objects, cards, or placards throughout a hospital environment. In one embodiment, each user can have a card, or codesheet, comprising that user's most commonly used codes. Thereby, the user only needs to scan the codes on their codesheet to enter particular data, or carry out specific instructions.

As described below, in addition to scanning in codes as data, the system also scans in codes that provide an instruction to the system. By scanning in a plurality of codes, a user, such as a nurse, can send messages, page, print, process commands at a server, and order medical tests. For example, in one embodiment, a nurse may need to page a doctor to the patient's location. In this embodiment, the nurse would scan the patient ID bracelet, which includes a scan code sequence identifying the patient. The nurse would then scan an instruction code, printed either on a placard or in the room, which provides the instruction "page the doctor". The scanned codes would be transmitted wirelessly to the server, and the instruction would be executed at the server.

The server would query a database or lookup table of codes and instructions for the scanned codes and determine that one of the scanned codes corresponded to a "paging" instruction. The system would then execute instructions to identify the doctor to be paged based on the scan code corresponding to the identification of the patient, and then page the appropriate doctor to the patient's location. In one embodiment, the system is linked to a hospital administration system which stores the name of each patient, and the doctor for the patient that is currently on-call. Thus, the wireless terminal not only provides the function of reading data with the code scanner, but also advantageously performs functions using the same code scanner.

The terminal preferably establishes communication with a server that maintains a database of codes and corresponding information or commands which it uses to process the codes received from the terminal via a wireless communication link. The server is preferably in communication with additional devices via a network, such as a local area network (LAN), where the additional devices perform a variety of functions, such as messaging, printing, or record keeping. The server is also configured to communicate with the wireless terminal to provide requested information or information in response to scanning of particular codes, such as codes corresponding to particular medications.

In one aspect of the invention, the wireless terminal has processing capabilities such that it can process codes locally without communicating with the server, and thereby interacting with the user autonomously in certain capacities. The terminal communicates with the user via indicators and a display screen, such as an LCD screen. The terminal can also be adapted with audio indicators such as a beep to indicate a warning condition or a message awaiting acknowledgement. The user can acknowledge or respond to messages displayed on the screen with an acknowledgement or "OK" button on the terminal. As one example, a nurse might scan in a code from a packet of Digoxin, which is a medicine to treat heart problems that should be administered only after an apical pulse measurement has been taken by the nurse. Once the nurse scans the code from the Digoxin packet, a processor in the terminal reads the code and compares it with an internal list of codes. In this case, the terminal would recognize the code as requiring an apical pulse measurement, and would display a warning and request input from the nurse of the apical pulse. The nurse could then scan in the apical pulse measurement by scanning codes corresponding to the appropriate numbers in order to enter the pulse measurement into the terminal. Once the pulse measurement was entered, the terminal could transmit the entered data to the server.

The codes used and maintained in the system are preferably in a "closed" symbology, such that only one code corresponds to a particular instruction or piece of information. This ensures that the system does not receive duplicate codes which correspond to different instructions or information. In certain embodiments, the codes are implemented as a 2-D matrix, or DOT as described in International Publication No. WO 02/07065, hereby incorporated by reference in its entirety. In one embodiment, the physical DOT is 7 mm in diameter, and comprises 321 white or dark hexagons. In another embodiment, the physical DOT is approximately 5 mm in diameter, but less than 7 mm in diameter. In one embodiment, a computer server can be configured to generate a 64 bit number, encrypt it, and algorithmically produce a 2-D DOT which uniquely represents the encoded data. Where the system is implemented using the DOT symbology, the system can have additional capabilities such as the methods and systems described in International Publication No. 02/21794 A2. As used herein, a "dot scanner" is configured to read the DOT symbology.

The 2-D DOT advantageously permits high density placement of DOTS as explained in Publication No. 02/21794 A2. The DOTS can be placed adjacent to one another in the same horizontal row or vertical column without the data from one DOT interfering with the ability of a terminal to read an adjacent DOT. Thus, the DOTS can be arranged as an array of DOTS. In one embodiment, a center to center distance between adjacent DOTS is approximately 20 mm and is less than 25 mm. In other embodiments, the center to center distance between adjacent DOTS is less than about 10 mm, 15 mm, 20 mm, 30 mm, 35 mm, 40 mm, 45 mm, 50 mm, 55 mm, 60 mm, 65 mm, 70 mm, 75 mm, 80 mm, 90 mm, or 100 mm.

Due to the vast number of data combinations made possible by the DOT symbology, (18 billion billion), an entire medical management system can be implemented using DOT's to represent all of the information and commands desired in the system. Thereby, the possibility of confusion with commonly used bar codes is eliminated. The system may, however, be implemented with both DOT and bar code technology, where the terminal would include both a bar code scanner and a DOT scanner. Such an embodiment is described below.

As used herein, "instructions" refer to computer-implemented steps for processing information in the system. Instructions can be implemented in software, firmware or hardware and include any type of programmed step undertaken by components of the system.

As used herein, a "code which corresponds to instructions" or a "code corresponding to an instruction" means a code that refers to, or is converted into, one or more instructions to be carried out in the system. For example, a code "ABC123" might point to an instruction that results in a doctor being paged to a particular room. Codes and their corresponding instructions can be stored in a database or lookup table so that scanning in a code causes the terminal to lookup the code in the database and retrieve its corresponding instruction, or set of instructions. As described, codes are preferably converted into 1D or 2D symbols so that they can be conveniently scanned into the system.

One example of a Local Area Network may be a corporate computing network, including access to the Internet, to which computers and computing devices comprising the system are connected. In one embodiment, the LAN conforms to the Transmission Control Protocol/Internet Protocol (TCP/IP) industry standard. In alternative embodiments, the LAN may conform to other network standards, including, but not limited to, the International Standards Organization's Open Systems Interconnection, IBM's SNA, Novell's Netware, and Banyan VINES.

As used herein, a "microprocessor" may be any conventional general purpose single- or multi-chip microprocessor such as a Pentium® processor, a 8051 processor, a MIPS® processor, a Power PC® processor, or an ALPHA® processor. In addition, the microprocessor may be any conventional special purpose microprocessor such as a digital signal processor or a graphics processor. The microprocessor typically has conventional address lines, conventional data lines, and one or more conventional control lines.

As used herein, the term "module" refers to the various modules in the system as discussed in detail below. As can be appreciated by one of ordinary skill in the art, each of the modules comprises various sub-routines, procedures, definitional statements and macros. Each of the modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

The system may include any type of electronically connected group of computers including, for instance, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI) or Asynchronous Transfer Mode (ATM). Note that computing devices may be desktop, server, portable, hand-held, set-top, or any other desired type of configuration. As used herein, an Internet includes network variations such as public internet, a private internet, a secure internet, a private network, a public network, a value-added network, an intranet, and the like.

As used herein, the term "programming language" refers to any programming language such as C, C++, BASIC, Pascal, Java, FORTRAN, and Assembly Language and ran under the well-known operating system. C, C++, BASIC, Pascal, Java, and FORTRAN are industry standard programming languages for which many commercial compilers can be used to create executable code.

System Overview

FIG. 1 is a block diagram of one embodiment of a medical management system 10 implemented in a hospital environment. The system comprises a computer or server 12, and a plurality of battery powered wireless terminals 14A-D, wherein the wireless terminals 14 and server 12 preferably communicate according to IEEE 802.11 wireless LAN specifications. The system can also use other wireless communications specifications known in the technology, such as radio frequency (RF) or Bluetooth. The system also preferably includes a hardwired terminal 16 coupled to the server 12 via a network or direct connection, wherein the hardwired terminal 16 can be used as a control point for the system such that only authorized users can activate a terminal 14A, and as a hardwired communication link between a terminal 14 and the server 12.

The wireless terminals 14 and server 12 preferably communicate periodically during communication sessions and are not in constant communication. Thereby, battery power at the wireless terminals 14 can be conserved and situations where the terminal 14 is out of communication range with the server 12 do not create power consuming loop processes wherein the terminal 14 continually attempts communication with the server 12. The server 12 and wireless terminals 14, however, can communicate at any instant if desired, and are not limited to communication during the designated communication sessions. The wireless terminals 14 are preferably small in size for ease of portability and one-handed use.

The server 12 is also coupled to a plurality of peripheral devices and systems, such as a printer 20, a messaging system 22, a pharmacy system 24, a laboratory system 26, a hospital server 28, and a patient record system 30, via a network connection. Commands or instructions received from the wireless terminals 14 are communicated by the server 12 to the various devices and systems for performance of requested tasks, and information from the various peripheral devices and systems are communicated to the wireless terminals 14 by the server 12. For example, the pharmacy system 24 can send updated medication information for patients or send notification to the server 12 when a patient's medication is ready. A terminal 14 can also query the pharmacy system 24 for information via the server 12. Similarly, a terminal 14 can send laboratory test requests to the laboratory system 26, or receive test results from the laboratory system 26 via the server 12.

Where the hospital server 28 maintains, for example, patient registration information, the hospital server 28 can send updated information to the server 12, and the wireless terminals 14 can update the hospital server 28, for example, when a patient has been discharged.

In one embodiment, the patient record system 30 is an Electronic Medical Record (EMR) system, and is updated with information from the wireless terminals 14 so as to maintain an electronic record of each patient's medication administration and any additional comments input to the terminal 14 by a user.

Thus, the wireless terminals 14 have capabilities similar to computer terminals which are connected to the peripheral devices and systems through a conventional network. The interaction of the wireless terminals 14, server 12, and peripheral devices and systems will be described in further detail hereinafter.

The server 12 comprises a database 32 for storing a plurality of scan codes and each codes' corresponding data or instruction in order to perform a plurality of electronic tasks. The data includes, for example, information corresponding to a patient, medication, objects, and note taking entries, and the instructions can include tasks such as "print a patient report", "order laboratory tests", and "request assistance". The database 32 can be modified and maintained using the terminal 16 or additional computer terminals in communication with the server 12. In certain embodiments, the system comprises both a local server and a remote server, including local and remote databases. In such embodiments, the local databases provide pointers to locate the appropriate remote server. In addition, where a plurality of servers and databases are used in a single hospital, for example, a master computer or server can be used to maintain and update the databases.

Server

Figure 2:
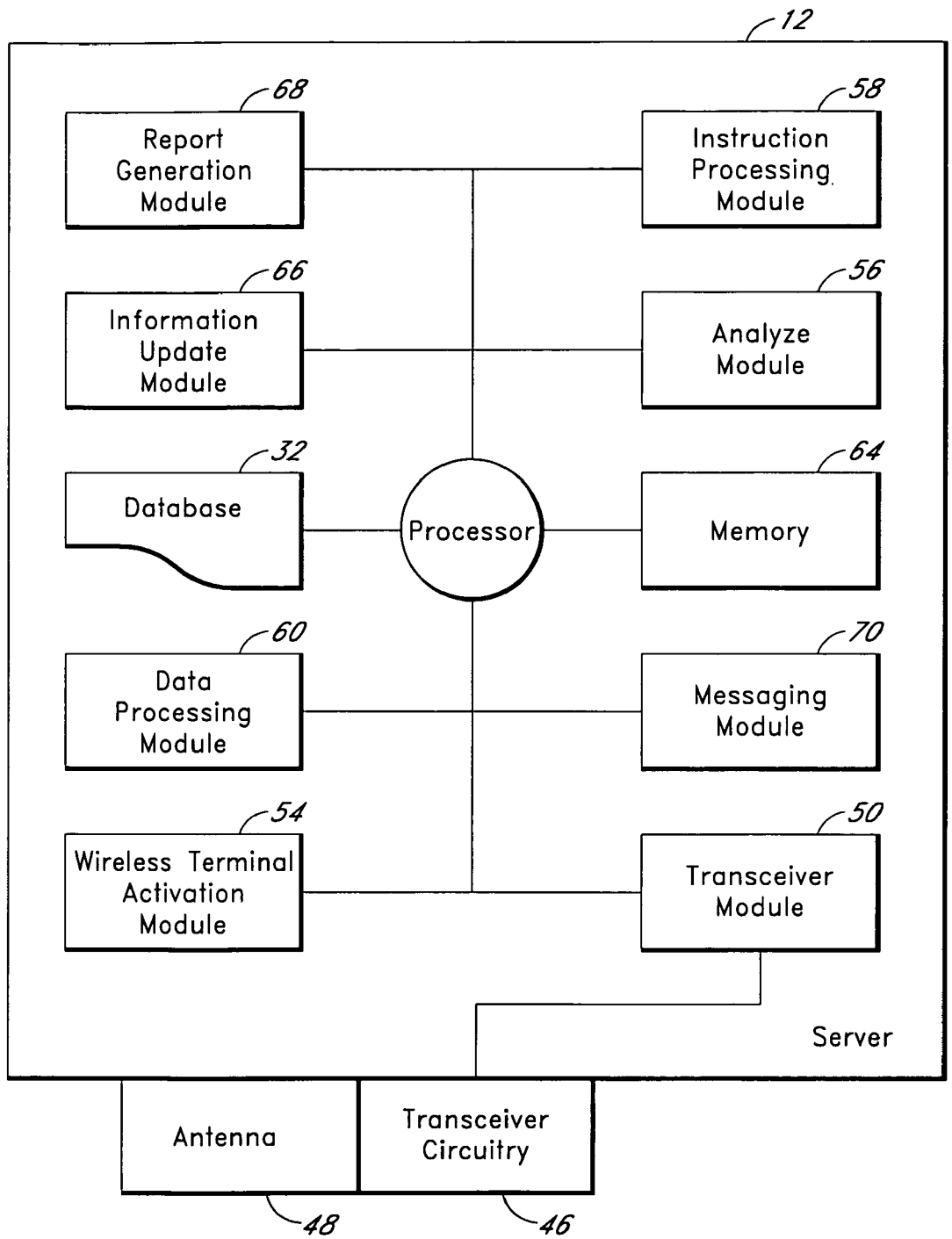
FIG. 2 is a block diagram of one embodiment of a server used in the medical management system shown in FIG. 1.

FIG. 2 is a block diagram of one embodiment of the server 12, wherein the server 12 is in data communication with transmit and receive, or transceiver circuitry 46 including an antenna 48 for wireless communication with the plurality of wireless terminals 14. The server 12 may include additional transmit and receive circuitry for processing of data and instructions where the server 12 is linked to a wireless access point including a transceiver and antenna. As described above, the server 12 can also communicate with the wireless terminals 14 via a hardwired connection at the hardwired terminal.

The server 12 comprises a transceiver module 50 configured to receive and facilitate transmission of data via the transceiver circuitry 46. The server 12 further comprises an activation module 54 configured to initiate each terminal 14 at the beginning of each use. In one embodiment, a user may request activation of a terminal 14 by scanning a code (or codes) corresponding to user information, such as a username and password. In one embodiment, the user scans an identification code on their name badge, and thereafter enters a password into the code scanner. In response to an activation request, the activation module 54 first verifies whether the user is authorized to use the terminal 14 by attempting to correlate the user information with information stored at the database 32. Secondly, where a nurse at a nurse's station in a hospital is requesting activation of the terminal 14, the activation module 54 sends a list of tasks to be performed and information to be used by the nurse during their working shift. More specifically, where Nurse A requests activation of a terminal 14, the activation module 54 sends information corresponding to Patients A, B, C, and D, who are assigned to Nurse A, to the terminal 14 along with any additional tasks to be performed by Nurse A for those patients or in general. These exemplary features of the system 10 are discussed in more detail hereinafter below in reference to FIGS. 12-13.

As shown in FIG. 2, the server 12 also comprises an analyze module 56 in data communication with the transceiver module 50 and configured to analyze incoming data or instructions from the wireless terminals 14 via the transceiver circuitry 46. The analyze module 56 is in data communication with additional processing and task performance modules at the server 12, and communicates the incoming data or instruction to the appropriate module according to its analysis. As will be appreciated by those skilled in the art, the server may include a separate analyze module or plurality of modules for analysis of data or instructions from the peripheral devices and systems and for analysis of data and instructions from the wireless terminals 14.

The server 12 further comprises an instruction processing module 58 for processing an instruction, and a data processing module 60 for processing data, wherein analysis by the analyze module 56 determines whether a communication from a wireless terminal comprises data or an instruction, and sends the communication contents to the appropriate module for processing. The server 12 also includes a processor 62 and a memory 64, used by instruction processing and data processing modules 58, 60 during operation. The memory 64 can also be configured to store the database 32 of scan codes and corresponding instructions or data. It should be realized that additional memory types, such as a flash memory, can also be used to store data within the server 12.

The memory 64 is also configured to store information received from the peripheral systems for use by the wireless terminals 14 and their users. For example, where a server 12 is assigned to each nursing station in a hospital, the memory 64 stores information corresponding to the patients assigned to the nursing station and the tasks to be performed by the caregivers assigned to the patients. More specifically, the medications, time of administration, and any additional information regarding the care of patient A is stored in memory 64 for use by the caregiver assigned to patient A.

The additional processing and task performance modules at the server 12 comprise an information update module 66, configured to update information stored in memory 64 with information from the plurality of peripheral devices and systems. For example, the information update module 66 receives medication orders from the pharmacy system, updates the memory 64 with the pharmacy orders, and sends updated medication orders to the appropriate wireless terminal 14.

As shown in FIG. 2, the server 12 further comprises a report generation module 68 configured to coordinate generation of a report for a particular patient or for all patients assigned to the user of the terminal 14 in response to an appropriate scan code instruction from a terminal 14. The report generation module 68 receives a report generation instruction from the instruction processing module 58, and uses the processor 62 and memory 64 to obtain the information to be included in the report. Once the information has been gathered, the report generation module 68 sends the report to the printer. This allows a user to scan a particular code on the terminal in order to have a predefined report printed from the data stored on the server or elsewhere.

In one embodiment, the server 12 also includes a messaging module 70 configured to receive, generate, and send messages to the wireless terminals 14 and peripheral systems. The module 70 receives messages from the messaging system 22 (FIG. 1) to be sent to the wireless terminals 14. The messaging system 22 can include a computer terminal, or plurality of terminals, where a user can enter a text message to be sent to a particular wireless terminal 14 by designating the user by name. For example, a text message comprising notification of an urgent telephone call can be entered at the hardwired terminal 16 for Nurse A. The messaging system 22 communicates the message and corresponding terminal user identification ("Nurse A", for example) to the server 12. The server 12 routes the message and user identification to the messaging module 70, which looks up the user identification (Nurse A) in the database 32 or memory 64 to determine which terminal 14 should receive the message. The messaging module 70 then formats the message for the destination terminal 14 and sends the message via the transceiver module 50 and transceiver circuitry 46 to the terminal controlled by Nurse A.

In one embodiment, the report generation module 68 is configured to generate a message to notify the user of the terminal 14 which requested generation of a report that the report has been printed. The generated message is communicated to the messaging module 70, which formats the message and adds information for communication to the appropriate terminal 14.

In another embodiment, the patient record system 30 maintains an electronic record for each patient with respect to medication administration, including, but not limited to, type of medication, quantity of medication administered, how administered, and time of administration. This information may then be stored at the server 12 and terminal 14, such that the server 12 may generate an alert or notification message if a terminal fails to timely send data indicating administration of medication. Alternately, the terminal may generate an alert or notification message if expected medication administration is not received by the stored time of administration, or within a predefined time period prior to the specified time of administration.

For example, a patient may be scheduled for administration of a particular medication at a predetermined time. The terminal 14 tracks an elapsed time after a predetermined medication administration time and may generate an alert or notification message if no indication of medication administration has been received within a predetermined alert time. The predetermined alert time may be, for example, 30 minutes or one hour after a scheduled administration time. Thus, the terminal 14 may be configured to monitor for an event where the time elapsed since the scheduled time exceeds some predetermined latency time. The terminal 14 may transmit the message to the server 12 for entry into the patient's care record. The terminal 14 will continue to periodically alert the user of the terminal 14 until the user acknowledges the alerts or the expected information is entered at the terminal 14. The user of the terminal 14 may acknowledge the alert or notification by, for example, selecting the "OK" button on the terminal 14.

Alternatively, the server 12 may send a message to a terminal 14 in response to some predetermined patient event. For example, a patient may have had one or more lab tests ordered to evaluate a condition. The server 12 may send a message to a terminal 14 in response to events such as availability of lab results for a particular patient, changes in patient medication, changes in patient health which may be monitored manually or through the use of telemetry, or some other predetermined event, such as a critical abnormal lab result.

In one embodiment, the server 12 maintains statistics on usage related to each individual terminal 14, the user, time information, and the type of code (barcode or DOT, for example) read by the user during each code read or scan event. In addition, information regarding, for example, mistakes in medication administration or user operation of the terminal, misreads of the code scanners, or other operational activity outside of an ideal work flow is tracked by the server. Such tracking or compilation of statistics provides for future performance improvement and optimization of the system.

Terminal

Figure 3:
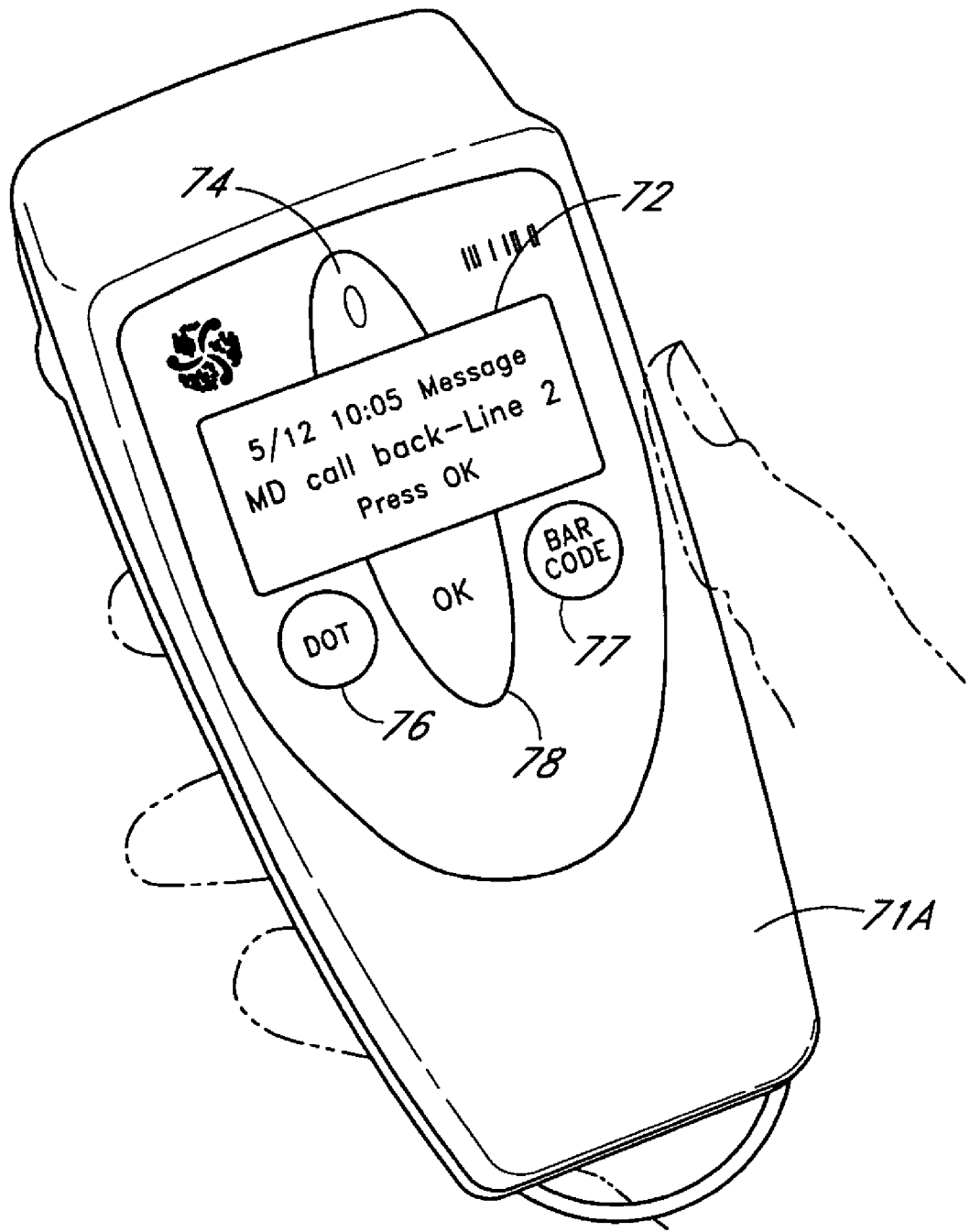
FIG. 3 is a perspective view of one embodiment of a wireless terminal according to one aspect of the invention.

FIG. 3 illustrates one embodiment of the terminal 14. As shown, the terminal 14 is designed to fit comfortably in one hand of a user. Moreover, the features of the terminal 14 are positioned so that the user can operate the terminal with one hand. An upper surface 71A includes a display 72, which is preferably a 3-line ×16 character backlit liquid crystal display (LCD). The display 72 can be used to display warnings, prompts, messages, etc., for the user. Of course, the invention is not limited to any particular type of display. Thus, display windows that show 1, 2, 4, 5 or more lines of text are within the scope of the invention. In addition, display windows that have additional features, such as chemiluminescent pigments, and non-textual display properties, are within the scope of the invention.

The terminal 14 may also include indicators, such as a multiple or tricolor LED "Good Read" and message indicator 74 which, for example, illuminates briefly in green to notify the user when a code has been properly scanned, illuminates in red to notify the user when a code has been improperly scanned, and illuminates in yellow to notify the user when a message has been displayed on the display 72. The terminal 14 may also include additional indicators, such as a power source indicator and a wireless connectivity indicator (not shown). Such indicators can be incorporated as part of the display 72, or can be separate LED indicators which illuminate only when the available power is low or the terminal 14 is out of range for wireless connection with the server 12. In other embodiments, the one or more indicators may be one or more LEDs. The indicators are not limited to the colors and functions described above. For example, an indicator LED may display red, yellow, or green, or combinations of these, depending on a status of the terminal 14.

Also located on the upper surface 71A is a DOT scan button 76 and a barcode scan button 77 to activate the code scanners, where the illustrated embodiment comprises both a DOT scanner and a barcode scanner. In the illustrated embodiment, the DOT scan button 76 is positioned on the upper surface 71A opposite the location of the DOT scanner on a lower surface of the terminal 14, and the barcode scan button 77 is positioned on the upper surface 71A opposite the location of the barcode scanner on the lower surface of the terminal 14 to indicate the location of the scanners to the user for scanning codes. It will be appreciated that in one embodiment a terminal comprises only a barcode scanner and barcode scan button, and in a second embodiment a terminal comprises only a DOT scanner and DOT scan button. The terminal may additionally or alternatively include means for reading an RF ID tag.

As shown, the terminal 14 also includes an "OK" or acknowledge button 78 for user input in response to questions, or to acknowledge messages appearing on the display 72. Engaging the OK button 78 allows the terminal 14 to interact with the user in a predefined manner so that input from the user can be stored within the terminal 14, or transmitted to the server 12 for processing. It should be realized that other mechanisms for entering data into the terminal 14 are also contemplated. For example, a pair of "YES" and "NO" buttons could be implemented in place of the single OK button 78. In addition, fewer or more buttons could be placed on the rear surface, or other surfaces of the terminal 14 without departing from the spirit of the invention. For example, the OK button 78 could be placed on a side surface and still be within the scope of the invention. In one embodiment, the terminal 14 includes a jog dial on a side surface of the terminal, for example, that can be used to scroll through messages that appear on the display 72, or to activate one of the scanners 80, 81.

Figure 4A:
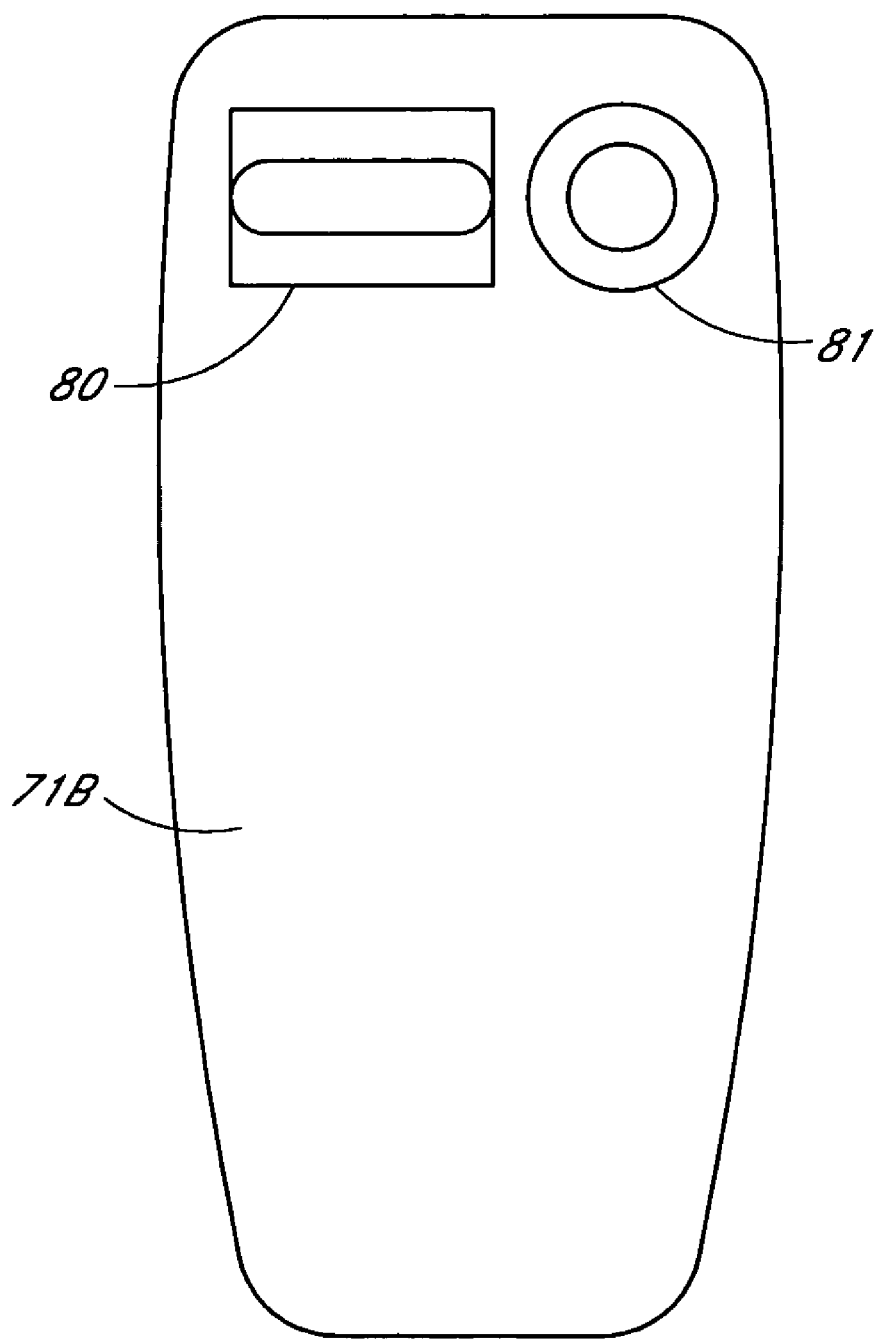
FIG. 4A is a bottom view of the wireless terminal shown in FIG. 3.
Figure 4B:
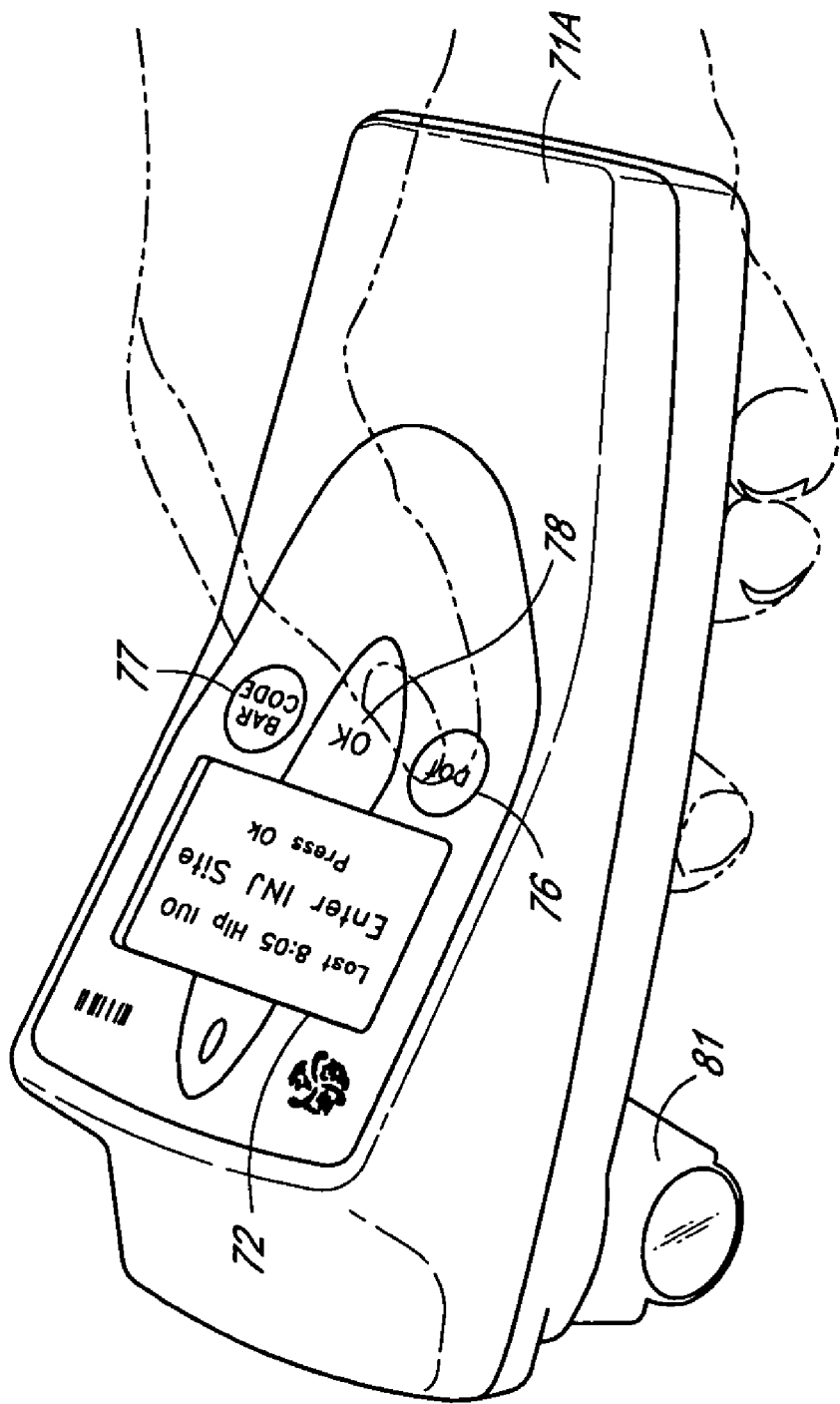
FIG. 4B is a side perspective view of the wireless terminal shown in FIG. 3.

FIG. 4A is a bottom view of the terminal 14 and shows a lower surface 71B which includes output windows for a bar code scanner 80 and a DOT scanner 81. Of course, embodiments of the invention include either fewer or more output windows for scanning codes into the terminal 14. In one embodiment, the terminal 14 only includes the bar code scanner 80. In a second embodiment, the terminal 14 only includes the dot scanner 81. FIG. 4B is a side perspective view of the terminal 14 and shows the upper surface 71A and a portion of the DOT scanner 81.

FIG. 5A is a block diagram of one embodiment of the terminal 14. As shown, the terminal 14 comprises the bar code scanner 80, DOT scanner 81, display 72, LED indicator 74, DOT scan button 76, barcode scan button 77, and acknowledge button 78. The terminal 14 further comprises a microcontroller 82, such as an Atmel AT91 16/32-bit microcontroller, which includes a processor 84. In one embodiment, the processor 84 has a 32-bit reduced instruction set computer (RISC) architecture with a 16-bit instruction set, for example, and is configured for low power consumption.

The microcontroller 82 further comprises memory, which may be a combination of a static random access memory (SRAM) 86 and flash memory 88. The SRAM 86 is configured to store program and application data, and preferably has a size capable of supporting a real-time operating system and application data, as well as memory space for image processing using data from the DOT scanner. In one embodiment, the SRAM 86 is supplemented by a pseudo SRAM device 87, which combines a dynamic random access memory (DRAM) cell structure with an SRAM interface, so as to provide for low power consumption and low device cost. As will be appreciated by those skilled in the art, the single communication lines connecting elements of the terminal 14 are exemplary in nature, and a plurality of communication or control lines are contemplated.

The flash memory 88 is configured for permanent storage of boot firmware, operating system, driver, protocol stack, and application programming, and is also preferably configured for low power operation. In one embodiment, the flash memory 88 provides a relatively small storage amount, such as 2 Mbytes, and additional flash memory 90 is provided external to the microcontroller 82. For example, an additional 4 or 8 Mbytes of flash memory 90 is mapped into the memory area of the microcontroller 82 using external interface or glue logic 92 for address decoding into the same bank as the flash memory 88. In one embodiment, the terminal operating system and/or application software at the flash memory 88, 90 can be upgraded in whole or in part via a wireless communication link.

The microcontroller 82 also comprises a plurality of interfaces for communication with a plurality of peripheral devices. In one embodiment, the microcontroller 82 further comprises an external bus interface 94 configured to interface with the external memory components 87, 90 and glue logic 92, for example. The microcontroller 82 may also comprise a plurality of universal asynchronous receiver-transmitters (UART's) 96, 97 configured for asynchronous communications with peripheral devices, a plurality of programmed input/output lines, and a programmed input/output controller 98, configured to control the signals on the parallel input/output lines according to information from the processor 84.

The terminal 14 may additionally comprise a supervisory chip 99 coupled to the processor 84 and including a reset function and a watchdog timer. The reset function facilitates a system reset, for example, when the voltage supply rail exceeds a predefined threshold and maintains the reset condition for a predefined period of time while the terminal 14 components are allowed to stabilize. The watchdog timer is coupled to a watchdog timer signal output from the processor 84, wherein the timer will trip in the event of a software deadlock at the processor 84, and subsequently initiate a system reset. In one embodiment, the terminal 14 includes a clock 100 which provides the CPU clock, and the processor 84 can be configured to reduce the clock rate to conserve power when in a standby or sleep mode. The clock 100 may include a clock synthesizer. The microprocessor 82 may also use the clock as a real-time clock in order to communicate reminder messages or tones to the user for scheduled medication administrations or tasks. The clock can also provide for time stamping of each code scanning event or other events at the terminal 14. The terminal 14 may also include a real time clock, such as the Real Time Clock chip DS2415 from Maxim Semiconductor (Dallas), to provide the microcontroller 82 with real time information.

The glue logic 92 is preferably provided by a low power complex programmable logic device (CPLD), and is configured to interface with the DOT scanner 81, a wireless communication transceiver 102, a display controller 104, and a user input and indicator controller 106. The terminal 14 may further include one or more antennas 108, coupled to the wireless communication transceiver 102. The DOT scanner 81 comprises an image sensor 120, such as an Omnivision OV6130 CMOS black and white imager incorporated into a digital camera including lens optics, and a bright LED 122 for illumination of the DOT image for scanning. In one embodiment, the DOT scanner 81 is a complete, individual unit and is configured to interface with the microcontroller 82 via the glue logic 92.

The wireless communication transceiver 102 is configured to communicate with the server 12 using wireless communication specifications such as RF, Bluetooth, or a WLAN specification, and the one or more antennas 108. In one embodiment, the wireless communication transceiver 102 is a wireless LAN (WLAN) module comprising a media access controller (MAC), such as the Agere WaveLAN WL 60010 MAC, and physical layer solution, such as the Agere WaveLAN WL 1141 802.11 b Physical Layer Solution. The MAC controller interfaces with the glue logic 92 via a compact flash interface 124, and implements the 802.11 protocol specified by IEEE standards. The WLAN module may also be configured to implement an advanced encryption standard (AES). In one embodiment, the terminal 14 further comprises an EEPROM 126, which is coupled to the transceiver 102 and configured to store device information, such as production attributes (serial number, board version, manufacturing date, MAC address, production number, etc.) and radio calibration data.

The display controller 104 is configured to interface with the display 72, which can be implemented with a black and white back-lit LCD. For example, the display 72 can be a 128×64 dot LCD module with chip-on-glass (COG) technology, or a 122×32 dot LCD module with tape carrier package (TCP) technology. The graphic controller 104 can be implemented, for example, with the Samsung Graphic Driver (KS0713/S6B1713). In one embodiment, the display controller 104 is not configured with built-in character fonts and a character font table is stored in memory in the terminal 14. The display controller 104 may be configured to display predefined symbols, such as a battery power indicator, battery charge status indicator, wireless communication status, and wireless communication signal strength.

In one embodiment, the user input and indicator controller 106 is configured to interface with one or more visual indicators, such as a plurality of single color LED's, bicolor LED's, or the tricolor LED indicator 74, so as to facilitate activation or illumination of such indicators according to control signals from the microcontroller 82. The user input and indicator controller 106 is further configured to monitor and receive input from one or more input switches or buttons, such as the DOT scan button 76, the barcode scan button 77, and the acknowledge or "OK" button 78. In one embodiment, the terminal 14 includes a jog dial switch to select and initiate the reading of a barcode or DOT image. The user input and indicator controller 106 preferably interfaces with the microcontroller 82 via the glue logic 92, wherein the glue logic 92 extends general purpose input/output (GPIO) capabilities from the microcontroller 82. In addition, a de-bounce function may be provided for the input buttons and the jog dial switch.

In one embodiment, the terminal 14 comprises one or more audio indicators, such as a piezo speaker 130 and driver 132, coupled either directly to the microcontroller 82 or through the glue logic 92. The audio indicator preferably provides acknowledgement to a user of a successful code reading and/or decoding of a barcode or DOT image, and may also notify a user of a waiting message, alarm, or warning. The audio indicator may also produce different audio signals to indicate different conditions to the user, such as a first audio signal to indicate a successful code reading and decoding, and a second, different audio signal to indicate an unsuccessful code reading and/or decoding.

The microcontroller 82 may include testing circuitry or one or more interfaces for testing circuitry at the terminal 14. In one embodiment, the microcontroller 82 comprises an embedded in-circuit emulator 134, and the terminal includes a joint test action group (JTAG) interface 136 to support ARM standard embedded in-circuit emulation. The terminal 14 may further comprise a debug port 138 for the microcontroller 82, comprising an RS232 transistor-transistor logic (TTL) interface to communicate with a peripheral test and debug monitor or circuit. The debug port 138 may also provide for initial programming of flash memory in the terminal 14 through a built-in flash programming routine at the microcontroller 82.

The terminal 14 further comprises the barcode reader 80, which may be implemented with a modular barcode scan engine such as a miniaturized, high performance 650 nm laser-based, single-line decoded scan engine from Symbol Technologies (model no. SE-923). The scan engine is preferably modular and self-contained, and includes a microcontroller configured to decode a barcode into a format compatible with and readable by the microcontroller 82. In one embodiment, the barcode reader 80 communicates with the microcontroller 82 through an RS232 TTL interface via a slave microcontroller 140. The slave microcontroller 140 is preferably configured for low-power operation, and acts as a pass-through device when the barcode reader 80 is configured to decode barcode data independently. In certain embodiments, the barcode reader 80 is implemented with a scan engine which is not configured to decode a barcode, and the terminal 14 further comprises additional decoding or conversion circuitry configured to convert barcode data into an acceptable format for processing at the slave microcontroller 140.

In one embodiment, the terminal 14 comprises a battery monitor and safety circuit 144 coupled to a battery power interface 146. The battery power interface 146 is preferably configured to draw power from a re-chargeable battery, such as a Li-Ion Polymer single cell battery, which provides approximately 3.7 volts. In one embodiment, the battery and the battery monitor and safety circuit 144 are a single unit, and may include the Texas Instruments chip BQ2050, for example. Where a re-chargeable battery is used, the terminal 14 further comprises a battery charger interface 148 configured to interface the battery monitor and safety circuit 144 with an external battery charger through metallic charger contacts, for example. The battery charger interface may be implemented, for example, with the Texas Instruments lithium ion charger, part no. BQ24002PWP.

The battery monitor and safety circuit 144 is configured to monitor the power level in the battery and conditions during charging, and the slave microcontroller 140 provides an interface, preferably a one wire interface, between the microcontroller 82 and the battery monitor and safety circuit 144. The battery preferably provides 3.3 volts for input/output and 1.65 volts for the processor core power rails through an on/off switch 149 for operation of the terminal 14. In one embodiment, the terminal 14 includes one or more voltage converters 150, such as the Micropower Synchronous Buck-Boost DC/DC converter by Linear Technology (LT3440EMS), to provide the desired power rails.

As the terminal 14 preferably remains operational for an extended period of time, such as up to 12 hours, the terminal 14 is configured for low power operation. In one embodiment, peripheral components of the reader are not all operated simultaneously. For example, the terminal 14 is preferably configured to refrain from transmitting and receiving data at the wireless communication transceiver 102 at the same time a code reading event occurs at the DOT reader 81 or the barcode reader 80. In certain embodiments, the wireless communication transceiver 102 may consume a large amount of power, and the specific transceiver implemented, such as the Agere WaveLAN, provides a variety of power savings modes that can be implemented to optimize the operational time of the terminal 14 between battery re-charging events.

Figure 5B:
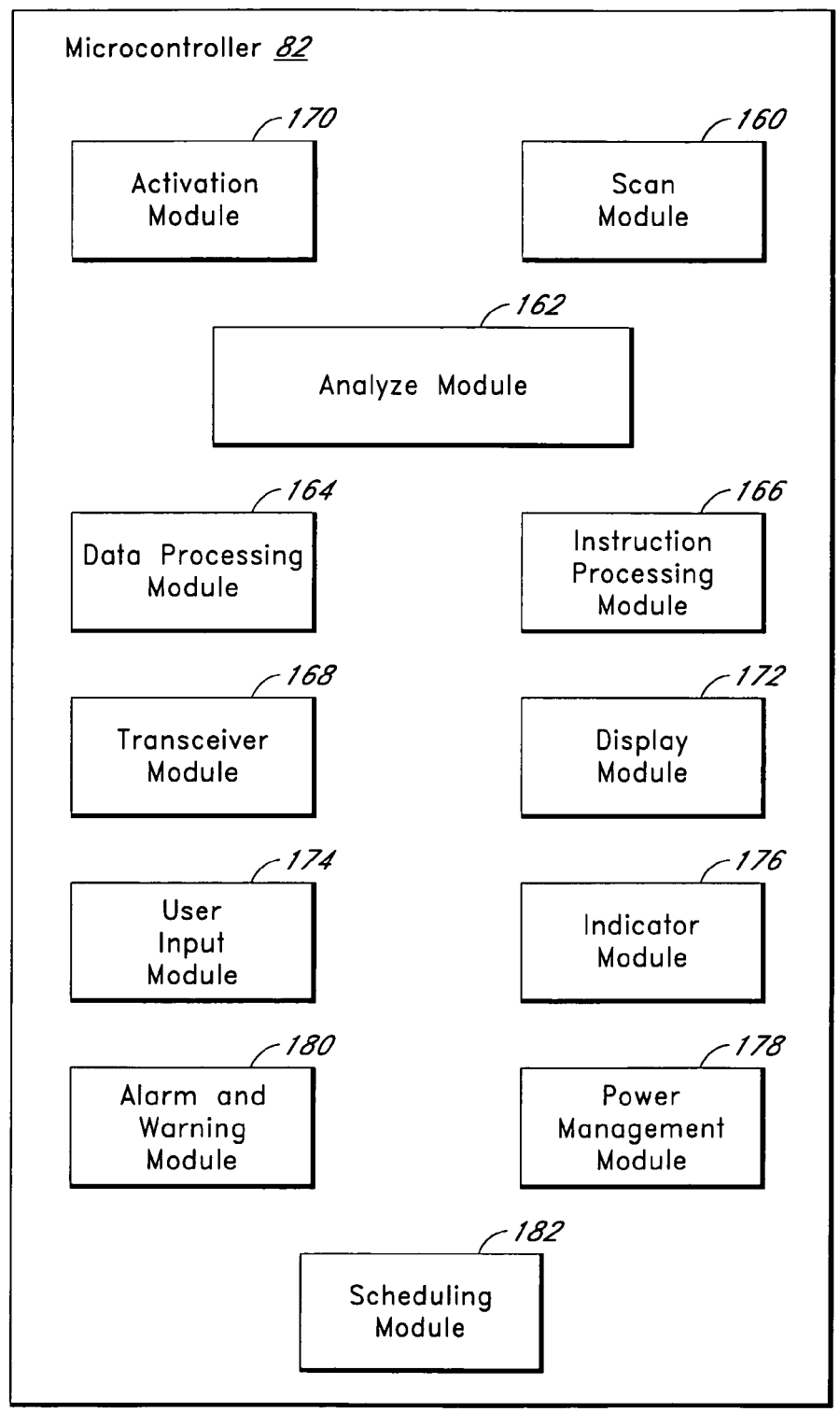
FIG. 5B is a block diagram of one embodiment of a plurality of modules communicating with the microcontroller of a wireless terminal.

FIG. 5B is a block diagram illustrating one embodiment of a plurality of modules for implementation at the microcontroller 82. As will be appreciated by one skilled in the art, the following described modules may be implemented in conjunction with processors and storage devices in addition to or in place of the microcontroller 82. As illustrated in FIG. 5B, the microcontroller 82 comprises a scan module 160 configured to process the codes read by the code scanners 80, 81, and an analyze module 162, configured to analyze the processed scan codes. The analyze module 162 is configured to determine, for example, whether a scan code corresponds to data or an instruction. If the analyze module 162 determines that a scan code corresponds to data, the data scan code is processed at a data processing module 164. If the analyze module 162 determines that a scan code corresponds to an instruction, then the instruction scan code is processed at an instruction processing module 166.

The data or instructions corresponding to the scan codes may be used or performed locally at the terminal 14, or transmitted to the server 12 via the communication transceiver 102. The microcontroller 82 may include a transceiver module 168, which is configured to format data or an instruction for communication to the server according to the communication specifications of the communication transceiver 102. As discussed above, the terminal preferably communicates with the server 12 during designated communication sessions. During a communication session, the terminal 14 preferably transmits more than a single scan code from the terminal 14, however, the terminal 14 can transmit a scan code outside a designated communication session according to whether the data or instruction is to be sent to the server immediately. Determination of whether data or instructions are to be transmitted immediately may be based on user input or the type of data or instruction.

The microcontroller 82 also comprises an activation module 170 configured to operate in conjunction with the activation module 54 at the server 12 when a user requests activation of a terminal 14. Following user authorization by the server 12, the activation module 170 is configured to process information sent by the activation module 54 at the server 12 and store the information in memory. In association with the modules illustrated in FIG. 5B, memory will be referred to generally and may include, but is not limited to, the SRAM 86 and Flash memory 88 at the microcontroller 82, and the additional pseudo SRAM 87 and Flash memory 90.

Referring to the example previously discussed, Nurse A requests activation of the terminal 14 by scanning a code on her identification badge. Upon authorization of Nurse A to use the terminal 14, which may also include input of a password at the hardwired terminal 16 or the terminal 14, the activation module 170 coordinates receipt of information corresponding to Patients A, B, C, and D, who are assigned to Nurse A, along with any additional tasks to be performed by Nurse A for those patients or in general. The activation module 170 then stores the received information in memory. The activation module 170 also stores the authorized user's identification code in memory, such that data and instructions sent to the server 12 can be tagged with the user's identification for future use, for example, in record keeping. In one embodiment, the terminal 14 communicates with the server 12 using a hardwired connection during an activation procedure.

The microcontroller 82 further comprises a display module 172 configured to facilitate display of messages, text, and indicators on the display 72 via the display controller 104. The microcontroller 82 also comprises a user input module 174, configured to monitor and process user input received at the OK button 78 and a keypad if included on the terminal 14. The user input module 174 responds to the received input accordingly, for example, depending on the message being displayed on the display 72.

The microcontroller 82 may further comprise an indicator module 176 configured to control illumination of the Good Read and message indicator 74, via the user input and indicator controller 106. As discussed above, the indicators may include an LED configured for illumination, for example, to notify a user that the terminal 14 is awaiting acknowledgment of a message or has displayed a warning at the display 72. The indicator module 176 may also be configured to facilitate illumination of the Good Read indicator 74 when either of the scanners 80, 81 have scanned a new code. Where the terminal 14 includes an auditory indicator, the indicator module 176 is further configured to facilitate activation of the auditory indicator, such as a beep or buzz, as a warning or to indicate that a code has been properly or improperly read by one of the scanners 80, 81. The terminal 14 can include a plurality of auditory indicators, which can be downloaded, for example, from the server 12 via a hardwired or wireless connection.

The microcontroller 82 also includes a power management module 178 configured to monitor remaining battery power via the battery monitor and safety circuit 14, and to schedule low power or no power operation of terminal components to conserve power. The power management module 178 may also be configured to facilitate display of the amount of available power or status of the battery via an indicator as discussed above. The power management module 78 may be further configured to facilitate communication of this information to the server 12. In one embodiment, the microcontroller 82 further comprises an alarm and warning module 180, configured to detect alarm and warning conditions and generate alarm or warning messages for display at the display 72, or activation of the indicators.

In the terminal 14 based embodiment of the alert system described above, the terminal 14 can further be configured maintain an electronic record for each patient with respect to medication administration, including, but not limited to, type of medication, quantity of medication administered, how administered, and time of administration. The microcontroller 82 may generate an alert or notification message if a user of the terminal 14 fails to timely indicate administration of medication. A user of the terminal 14 may timely indicate administration of medication by, for example, reading the DOTs associated with the patient and the medication. The microcontroller 82 may include a scheduling module 182 configured to manage scheduled tasks such as medication administration times, to monitor user input indicating completion of scheduled tasks or rescheduling thereof, and user notification of scheduled tasks.

For example, a patient may be scheduled for administration of a particular medication at a predetermined time. The terminal 14, uses a schedule monitoring function at the scheduling module 182 to track an elapsed time after a predetermined medication administration time and may generate an alert or notification message if no indication of medication administration has occurred within a predetermined alert time. As with the server based system, the predetermined alert time may be, for example, 30 minutes or one hour after a scheduled administration time. Thus, the scheduling module 182 may monitor data entry for receipt of scan codes indicating administration of a medication or completion of a task, for example, which correspond to scheduled medication administrations or tasks. In the event the scheduling module 182 determines that the elapsed time following a scheduled medication administration exceeds some predetermined latency time, and no scan codes have been received to indicate completion of the scheduled medication administration, the scheduling module 182 facilitates activation of an indicator or display of an appropriate message at the display 72. The terminal 14 may continue to periodically display or sound the notification or alert until acknowledgement by the user of the terminal 14. The user of the terminal 14 may acknowledge the alert or notification by, for example, selecting the "OK" button 78 on the terminal 14 or by performing the process associated with the alert. The terminal 14 may present the alert on a display, using one or more indicators, audibly, or using some other way or some other combination of ways.

In one embodiment, the terminal 14 is configured to schedule notification for a follow-up task in response to an event such as administration of a medication or treatment. For example, in response to receipt of user input indicating administration of a medication, the scheduling module 182 schedules a follow-up visit notification or reminder for the user to visit the patient and perform an additional task. In one particular example, a nurse may administer a pain medication and input corresponding information into the terminal 14. In response to receipt of information regarding the administration of the pain medication, the scheduling module 182 schedules a notification for a predetermined time following administration of the medication, such as one hour. In addition, the notification may include instructions to perform an additional task or enter additional information, such as patient heart rate or a pain score provided by the patient. Subsequently, the terminal 14 notifies the user, upon lapse of the predetermined time, with instructions to visit the patient and perform a predetermined task or obtain and input predetermined information or data, such as a pain score.

Processes

Figure 6:
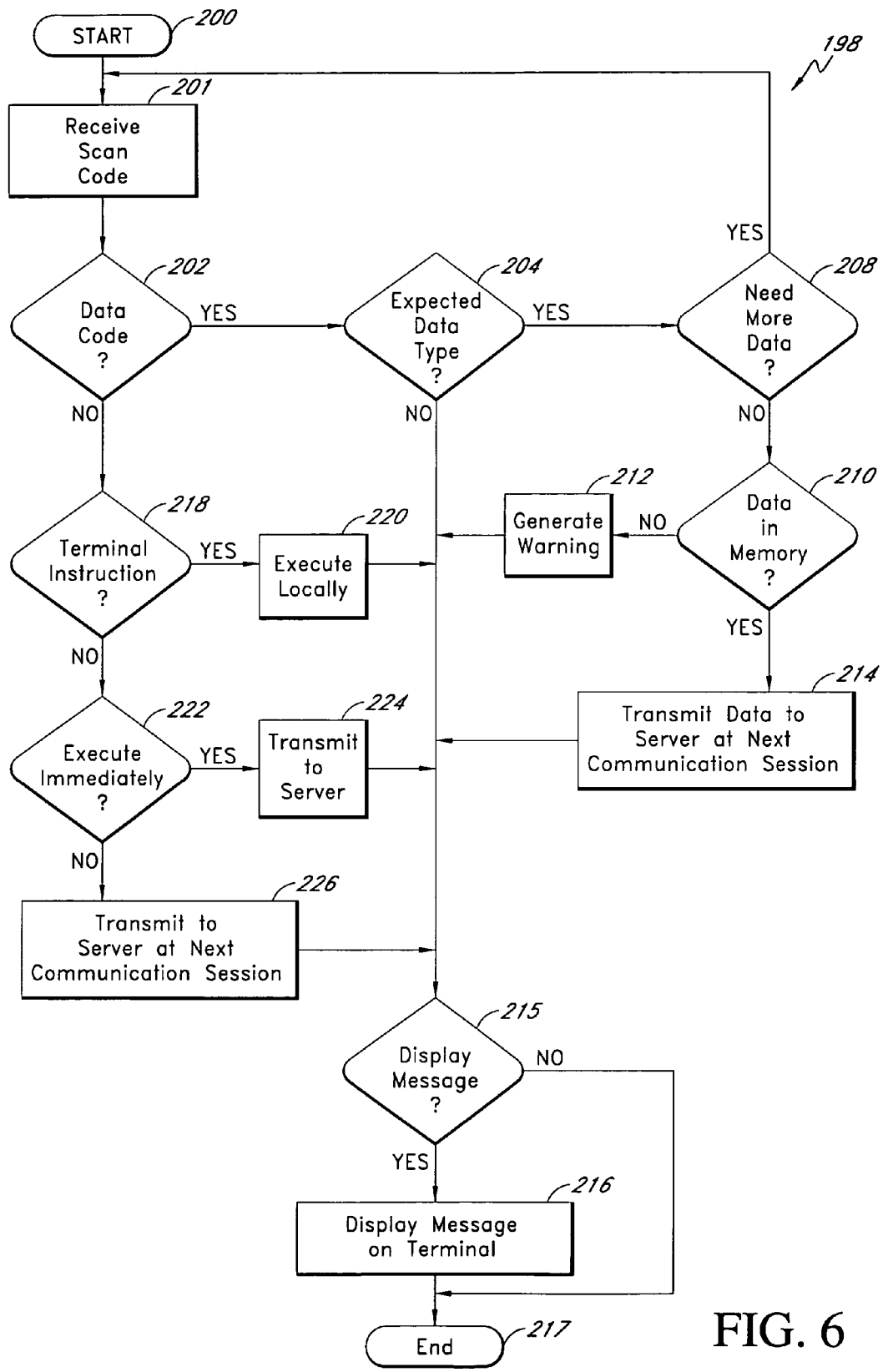
FIG. 6 is a flowchart illustrating one embodiment of a method of operating a wireless terminal in the medical management system.

One embodiment of a method 198 of operating the terminal 14 is illustrated in the flowchart of FIG. 6. The process begins at a start state 200, and then moves to a state 201 wherein the terminal 14 receives a scan code using one of the scanners 80, 81. In a state 202, the terminal 14 determines whether the scan code corresponds to data or an instruction, wherein such a determination can be made according to a single bit in the scanned code, for example. If the terminal 14 determines that the scan code corresponds to data in state 202, the terminal 14 determines whether the data is the type of data expected in a state 204. For example, where the previous code scanned by the terminal 14 corresponds to a patient and the terminal was awaiting a scan code corresponding to a medication or note taking entry for the patient, the wireless terminal would recognize that the current scan code corresponding to a different patient was not expected.

If the scan code is determined to correspond to an expected type of data as determined in state 204, the terminal 14 determines whether to wait for additional data in a decision state 208. If the terminal 14 determines that it should wait for additional data in state 208, the wireless terminal waits to receive another scan code in state 201. For example, where a scan code corresponding to patient identification data was received in state 200, the terminal 14 would await additional data for the patient, such as the medication administered, dosage of medication, and note taking entries.

In the event the terminal 14 determines in decision state 208 that it should not wait for additional data, it proceeds to a state 210 to determine whether the scan code data corresponds to data stored in memory. For example, where the authorized medications for Patient A are stored in memory, the terminal 14 determines whether the scan code data corresponds to an approved medication for a designated patient as stored in memory. If the scan code data does not correspond to the data in memory, the terminal 14 generates a warning to the user in a state 212, indicating that a code corresponding to an incorrect medication has been scanned. The terminal 14 waits to receive another scan code in state 201. The process 198 then moves to decision state 215 to determine whether or not to display the warning to the user. If a warning is to be displayed, the process 198 moves to state 216 and displays the message at the display 72. If a determination is made at decision state 215 that no warning is to be displayed to the user, the process skips state 216 and terminates at an end state 217.

However, if the scan code data does correspond to an authorized medication in state 208, the wireless terminal transmits the scan code data to the server at the next communication session in state 214. Preferably, a plurality of scan codes are grouped together for transmission to the server, wherein a group comprises a patient identification code, a medication code, and a dosage. Depending on the type of medication administered, the group may also comprise a patient's vital sign such as temperature, method of administration such as oral or injection, and location of injection. Of course, embodiments of the invention are not limited to particular groupings of data for transmission to the server.

If the scan code is determined to correspond to an unexpected type of data as determined in state 204, the method 198 then moves to decision state 215 to determine if a message should be displayed to the user. There are several instances where the user should be provided with messages. For example, where the terminal 14 is being used to document and ensure accurate medication administration, the user first uses the wireless terminal to scan a code corresponding to a patient, such as a code on the patient's wristband. In response to such a code, the terminal 14 waits for additional data, and the user would proceed to scan a code on medication packaging. The wireless terminal 14 then uses the patient identification code to determine whether the code from the medication packaging is an authorized code for the patient according to the information stored in memory. In the event the scanned medication code corresponds to the authorized medication as stored in memory, the terminal 14 may display a message to indicate that the administration of the medication is authorized, dosage information, and administration information. The terminal 14 can also display a prompt to the user for entry of additional information, such as patient pulse and/or temperature. The user can enter such additional information, for example, by scanning codes corresponding to numerical digits with the terminal 14.

Following administration of a medication, a caregiver can use the terminal 14 for documentation or note taking. In particular, the user can document a reaction to a medication by scanning the appropriate code. For example, in the event a patient vomits after receiving medication, the user of the wireless terminal scans a code corresponding to the text "PATIENT VOMITED". The terminal 14 recognizes that the code corresponds to documentation data and transmits it to the server 12 with the patient identification code during the next communication session.

Referring now back to decision state 202, if the terminal 14 determined that the received scan code corresponds to an instruction, the terminal 14 proceeds to a decision state 218. In decision state 218, the terminal 14 determines whether the instruction is to be performed by the terminal 14 or to be sent to the server 12. If the instruction is to be performed by the terminal 14, the wireless terminal executes the instruction in a state 220. The process 198 then moves to the decision state 215 to determine if a message should be displayed to the user.

If the instruction is to be sent to the server 12, the terminal 14 proceeds to a decision state 222 to determine whether the instruction is an immediate instruction, i.e. the instruction needs to be sent immediately and the terminal 14 should not wait for the next communication session. If the terminal 14 determines that the instruction is an immediate instruction in state 222, the terminal 14 transmits the instruction to the server 12 immediately in a state 224 and does not wait for the next communication session. If the wireless terminal determines that the instruction is not an immediate instruction in state 222, the terminal proceeds to a state 226 to transmit the instruction to the server 12 during the next scheduled communication session.

Thus, in one embodiment, the user of the terminal 14 scans a code corresponding to an instruction to print a report or order a laboratory test for a patient, sends a message or page, or requests information from a peripheral system connected to the server 12 by scanning the appropriate code(s) with the code scanners 80, 81. The terminal 14 then proceeds to transmit the instruction and any additional information, such as patient identification information, to the server 12 to initiate a procedure according to the instruction.

The terminal 14 can also initiate performance of an instruction, such as immediate request for assistance. For example, a user can scan a code on the wall in a patient room to request immediate assistance, wherein the code includes information regarding the location of the code as scanned. Such an instruction would be determined to be an immediate instruction in state 222 and would therefore be transmitted to the server 12 without waiting for the next communication session. In addition, the terminal 14 is configured to execute instructions or commands such as display medication data for a patient, or recall and display the last N scan code entries.

Transmitting Data

Figures 7, 8:
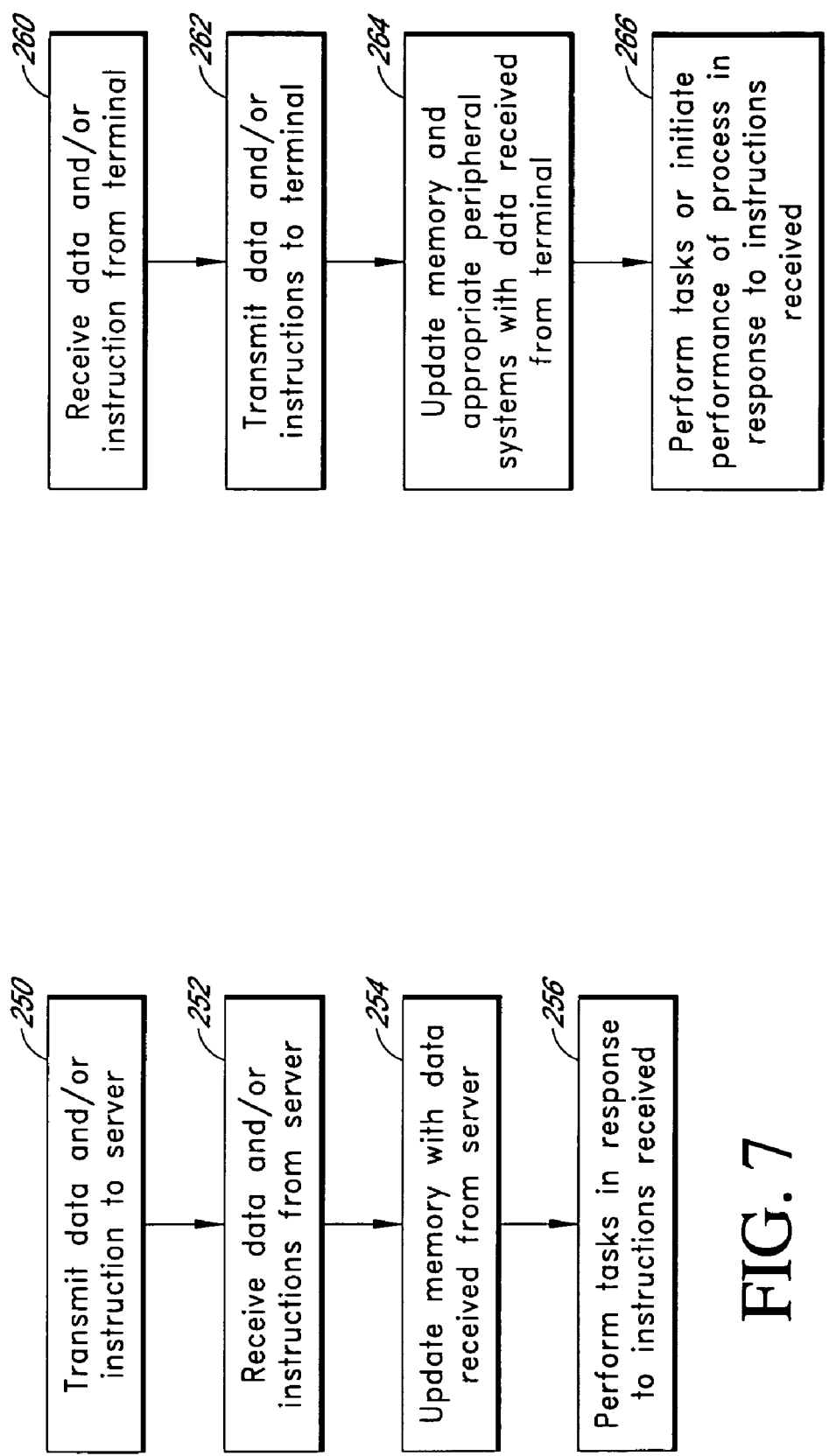
FIG. 7 is a flowchart illustrating one embodiment of a method of operating a wireless terminal during a communication session with the server.
FIG. 8 is a flowchart illustrating one embodiment of a method of operating the server during a communication session with a wireless terminal.

FIG. 7 is a flowchart illustrating one embodiment of a method of operation of a terminal 14 during a communication session. In a state 250, the terminal 14 transmits data and/or instructions to the server 12. In a state 252, the terminal 14 receives data and/or instructions from the server 12, and in a state 254, the terminal 14 updates memory with the data received from the server 12. In a state 256, the wireless terminal 12 performs the instructions received from the server 12, such as display of a message on the display 72.

One embodiment of a method of operation of the server 12 during a communication session with a wireless terminal is illustrated by the flowchart of FIG. 8. In a state 260, the server 12 receives data and/or instructions from the terminal 14, and in a state 262, the server 12 transmits data and/or instructions to the terminal 14. In a state 264, the server 12 updates memory 64 and the appropriate peripheral systems, such as the patient record system 30, with the data received, and in a state 266, the server 12 performs tasks or initiates performance of a process in response to instructions received from the wireless terminal 14.

Processing Data and Instructions

Figure 9:
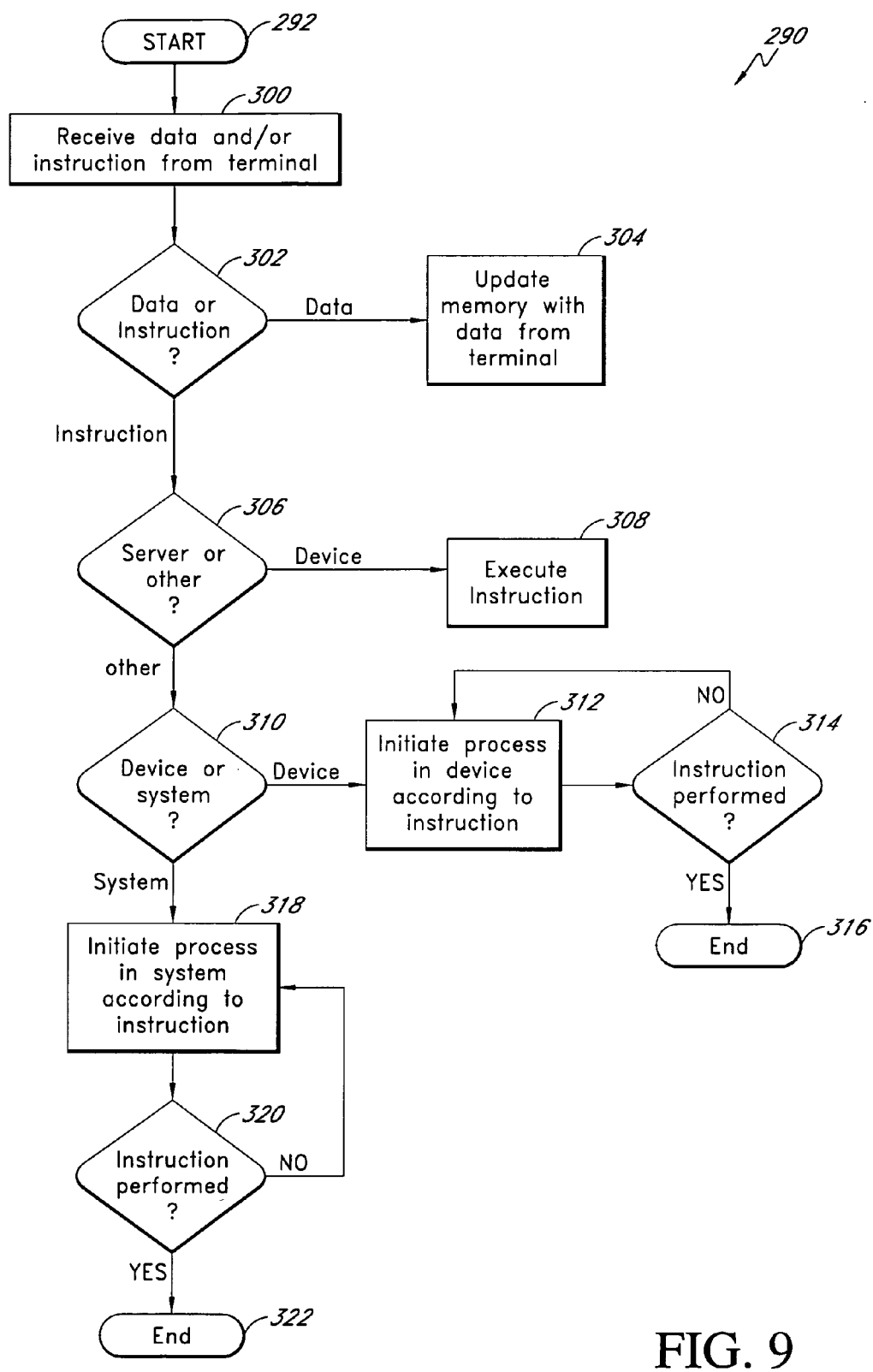
FIG. 9 is a flowchart illustrating one embodiment of a method of operating the server.

One embodiment of a method 290 of operation of the server 12 in response to receiving a scan code from a terminal 14 is illustrated in more detail in the flowchart of FIG. 9. As illustrated in FIG. 9, the method begins at a start state 292, and proceeds to a state 300 wherein the server 12 receives data and/or an instruction from the terminal 14 in the form of a scan code. In a state 302, the server determines whether the scan code corresponds to data or an instruction. If the scan code corresponds to data, the server 12 proceeds to a state 304 wherein memory 64 is updated with the data. The server 12 may also send the data to the appropriate peripheral system such as the patient record system 30.

If the scan code is determined to correspond to an instruction in state 302, the server proceeds to a state 306 to determine whether the instruction is to be performed by the server 12 or another device or system. If the instruction is to be performed by the server 12, the method proceeds to a state 308 wherein the server 12 executes the instruction. If the instruction is to be performed by a device or system other than the server 12, the server 12 proceeds to a state 310 to determine whether the instruction is to be performed by a peripheral device, such as the printer 20, or a system, such as the messaging system 22.

If the instruction is to be performed by a device, the server 12 proceeds to a state 312 where the process is initiated in the designated device according to the instruction by either sending the instruction directly to the device, or modifying and formatting the instruction and sending a formatted instruction to the designated device. Following initiation of the process in the designated device, the server 12 may query whether the instruction has been performed or completed in a state 314. If the instruction has not been performed, the server 12 can initiate the process in the designated device again by returning to state 312. If the instruction has been performed, the server 12 proceeds to an end state 316. In addition, the server 12 can send a message to the terminal 14 notifying the user that the process initiated in response to the received instruction has been completed.

If the server 12 determines in state 310 that the instruction is to be performed by a system, the server 12 initiates the appropriate process in the designated system or sends the instruction to the system designated as part of the instruction. In a state 320, the server 12 queries the system as to whether the instruction has been performed. If the instruction has been performed, the server proceeds to an end state 322, and if the instruction has not been performed the server returns to state 318 and sends the instruction to the designated system again to be performed. Alternately, if the instruction is in the process of being performed, or is waiting to be performed, the server 12 will continue to query the system until the instruction has been performed. In addition, the server 12 can notify the user of the terminal 14 that sent the instruction that the instruction has been performed by sending a message to the terminal 14 for display.

Information Update Module

Figure 10:
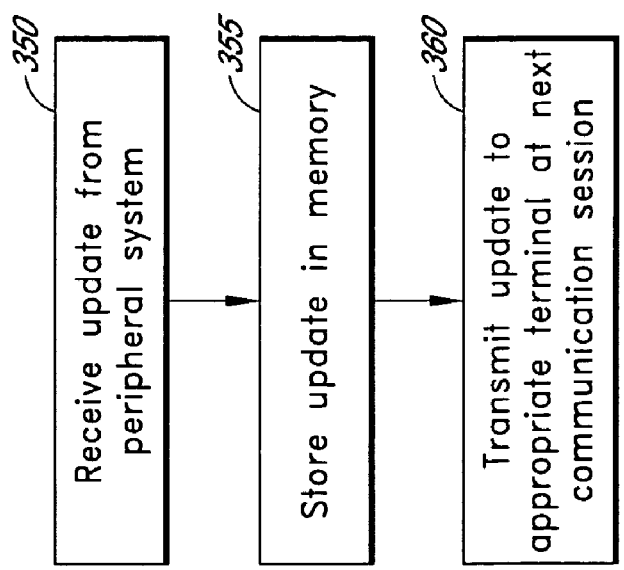
FIG. 10 is a flowchart illustrating one embodiment of a method of operating the information update module in the server.

FIG. 10 is a flowchart illustrating one embodiment of a method of operation of the information update module 66 in the server 12. In a state 350, the server 12 receives an information update from a peripheral system or device, such as the pharmacy system 24, wherein the information received comprises updated medication orders for a patient or medication orders for a new or transferred patient. In a state 355, the information update module 66 stores the information in memory 64, and transmits the updated information to the appropriate terminal 14 during the next communication session.

Messaging Module

Figure 11:
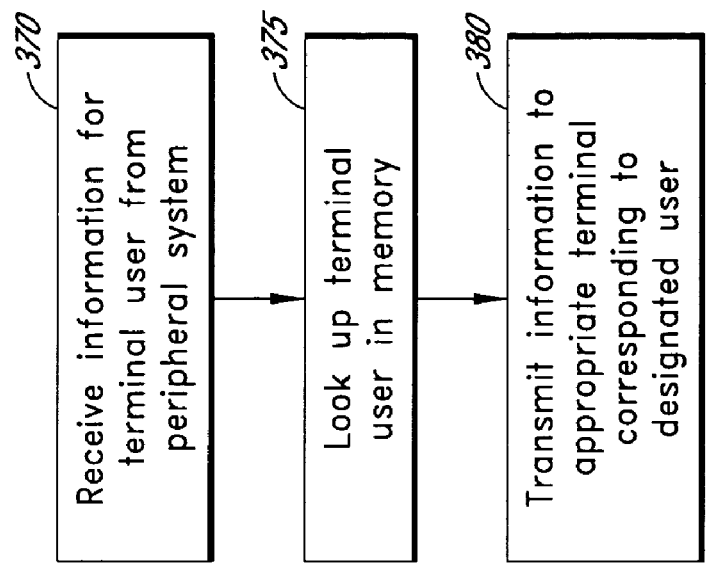
FIG. 11 is a flowchart illustrating one embodiment of a method of operating the messaging module in the server.

One embodiment of a method of operation of the messaging module 70 in the server 12 is illustrated in the flowchart of FIG. 11. The messaging module 70 receives information including a message for a terminal 14 user in a state 370. In a state 375, the messaging module 70 looks for the terminal user, designated by name or ID number, in memory 64 and determines which terminal 14 to send the message to according to user information for each terminal 14 stored in memory 64. In a state 380, the messaging module 70 transmits the message to the appropriate terminal 14 using the transceiver 46 and antenna 48.

The system 10 is also capable of additional processes, such as billing or inventory control. For example, every item given or used by a patient in a hospital has a scan code applied to it or that corresponds to it in the system. When that item is used by or for the patient, the caregiver providing the item scans the patient ID code and the item code. Such information is then transmitted to a billing or record keeping system for future reference.

An additional capability of the system 10 may include entry of physician orders for patients, where a physician uses a terminal 14 to enter medication or medical care orders for a patient by scanning codes corresponding to the patient identification information, the medication to be administered, the dosage, and additional information regarding administration of the medication.

Example Process

FIG. 12 is an example of a Medication Worksheet 1200 that may be used in conjunction with a terminal 14 and server 12, operating in a system such as the hospital system 10 of FIG. 1, and using, for example, the processes of FIGS. 6-11. In one embodiment, a user such as a nurse, authorized personnel, or system administrator obtains a printed version of the Medication Worksheet 1200 at the beginning of a working shift. For example, as previously discussed, the user of a terminal 14 may scan a code corresponding to an instruction to print a Medication Worksheet, and then scan a code corresponding to data identifying the user. In response to the instruction, the server 12 would facilitate printing of the Medication Worksheet for the identified user.

The Medication Worksheet 1200 comprises a number of fields supplying a variety of information. For example, the Medication Worksheet 1200 can include an assignment field 1210 that identifies the responsible user or nurse, applicable date, and applicable shift in terms of time. The Medication Worksheet 1200 can also include a patient field 1220 that identifies one or more patients, their corresponding medications, and scheduled administration times for the medications.

The Medication Worksheet 1200 can also include fields comprising scan codes that a user such as a nurse or authorized personnel are likely to use during their working shift, such as medication administration sites. In one embodiment, the fields include a "sites" field 1230, an "override" field 1240, a "keypad" field 1250, and an "other" field 1260.

The "sites" field 1230 can include one or more scan codes associated with one or more medication administration sites or methods. For example, a user can administer medication to a first patient in accordance with the schedule shown in the patient field 1220, wherein the user scans a first patient scan code 1222 associated with the first patient. The user can then indicate, by scanning the appropriate scan code, the site at which a first listed medication was administered. For example, the user may scan the "1. thigh" scan code 1232 to indicate that the first medication was administered via an injection to the left thigh. The terminal 14 would then transmit the information corresponding to the scan codes, such as patient information, medication, and location of medication administration, to the server 12. In response to receipt of the information from the terminal 14, the server 12 can then communicate the information to one or more modules or servers in the system, such as the patient record system 30.

The user can similarly scan a scan code in the "override" field 1240 to indicate a reason for overriding a scheduled administration of medication, such as "increased nausea". The "keypad" field 1250 can be used to compose messages or enter data for transmission to a server 12, such as patient statistics including temperature. In FIG. 12, the keypad field 1250 shows a numeric keypad. In other embodiments, the Medication Worksheet 1200 may include a numeric, alphanumeric, symbolic, combination thereof, or some other keypad.

The "other" field 1260 can include other instructions or data entries not included in the previously described fields. For example, the "other" field 1260 may include a page scan code 1262 corresponding to an instruction to "page S. Felner RN", or other designated personnel that may be currently on duty. In response to a user scanning the page scan code 1260, the terminal 14 sends an instruction to the server 12, and the server facilitates a page to the listed party. In addition, the user can compose a message that is used in the page using the scan codes in the "keypad" field 1250, or additional scan codes in the "other field 1260 corresponding to predefined messages, such as "patient requested consultation".

It may be advantageous to implement the scan codes on the Medication Worksheet with DOTs to identify various inputs. Unlike a bar code, the DOTs consume a small area on a standard printed page and can be positioned adjacent one another, both horizontally as well as vertically. The 2-dimensional nature of the dots allows the terminal 14 to isolate and selectively read dots that are positioned very close to one another.

Figure 13:
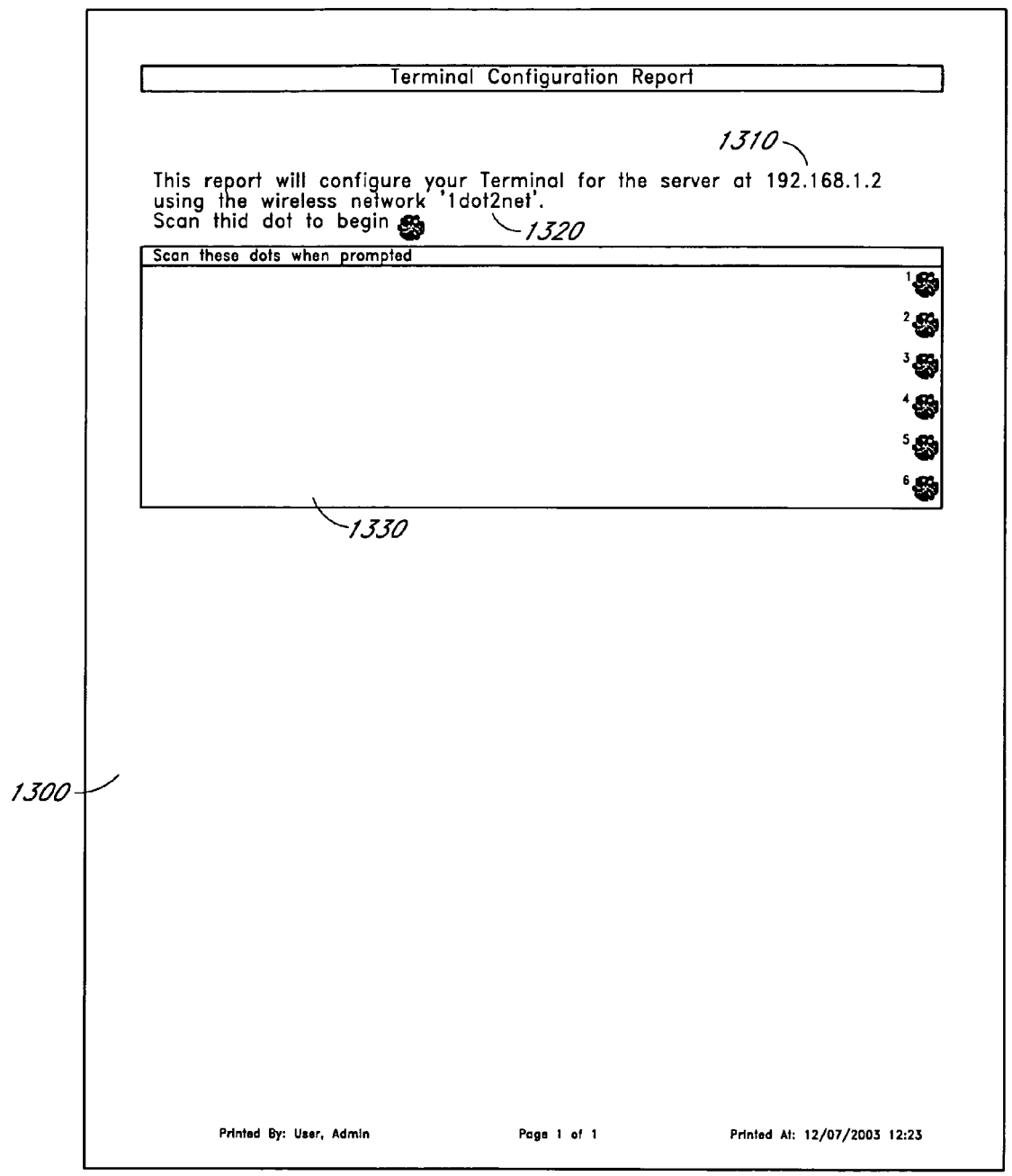
FIG. 13 is an exemplary illustration of one embodiment of a configuration report used to configure a wireless terminal.

The system 10 can similarly use DOTs to initially configure a terminal 14. FIG. 13 shows an embodiment of a configuration report 1300 that can be generated and used to configure a terminal 14. A system administrator or other user can input information to the server 12, at the hardwired terminal 16, for example, and can thereby facilitate printing of the configuration report 1300 by the printer 20 (see FIG. 1).

The user can then configure the terminal 14 using the information provided in the configuration report 1300, such as written instructions and a plurality of scan codes implemented with DOTs, barcodes, or a combination thereof.

In one embodiment, the system administrator inputs a server address 1310 and network address 1320 to the server 12. The server address can be, for example, an IP address. The system administrator can, for example, identify one of a plurality of server addresses using a pull down menu, manual entry, automated process or some other method of identifying a server. Similarly, the system administrator can identify a network from one or more available networks using a pull down menu, manual entry, automated process or some other method of identifying a server 12.

The server 12 can then process the information entered by the system administrator and generate one or more configuration scan codes 1330 that can be used to configure the terminal 14. The one or more scan codes 1330 can include, for example, one or more DOTs that identify or dictate a configuration operation recognized by the terminal 14. One or more additional scan codes may also be used to identify the server address and network, as well as other communication protocol. In one embodiment, the one or more scan codes in the configuration report 1300 identify a Wired Equivalent Privacy (WEP) algorithm key that is used by the terminal 14 to provide security over a wireless communication channel.

In order to configure a terminal 14 using the configuration report 1300, a user can simply sequentially read each scan code or DOT in the configuration report with the terminal 14. The terminal 14 is configured once all of the dots in the configuration report 1300 have been read by the terminal 14.

Exemplary DOT Scanner

Figure 14A:
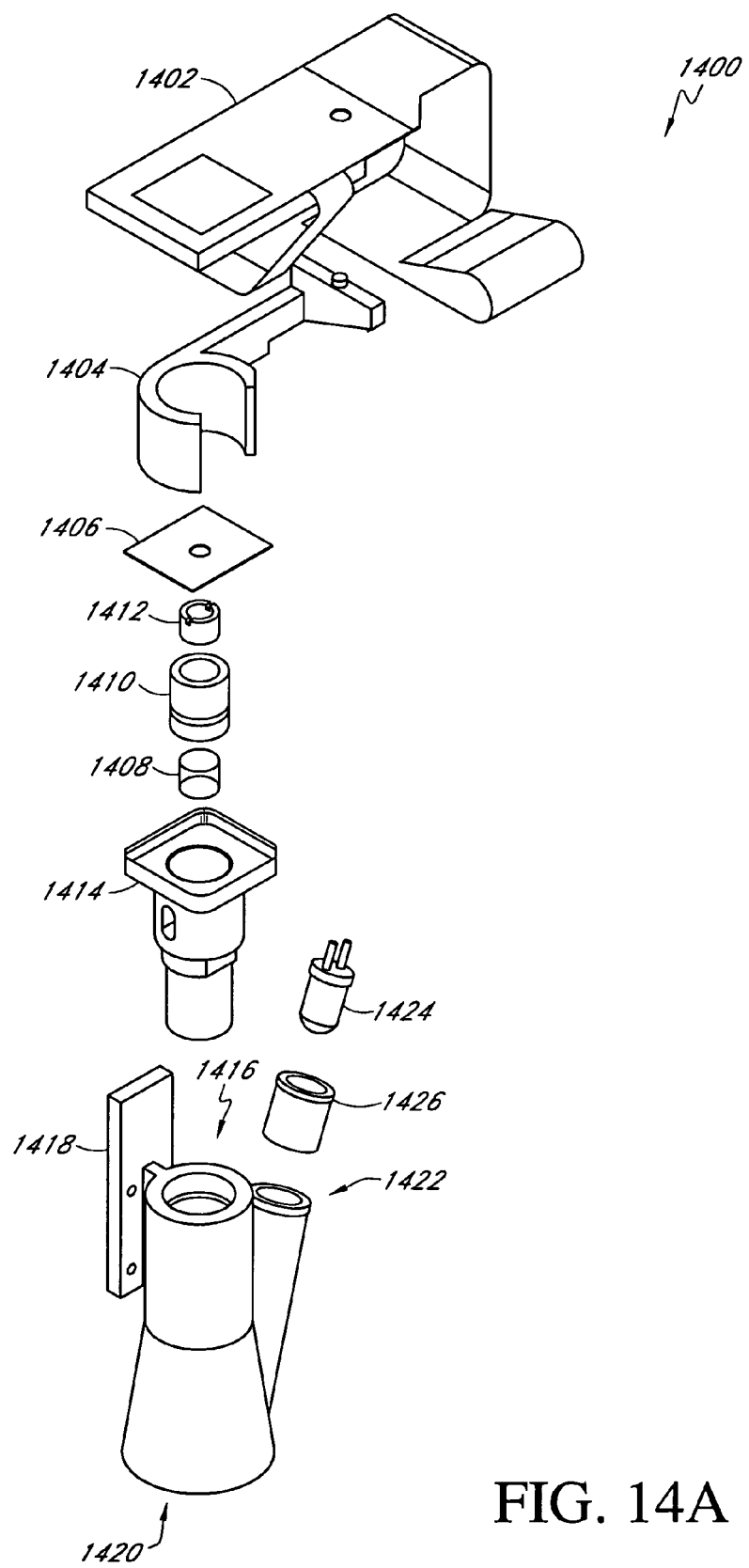
FIG. 14A is perspective assembly view illustration of one embodiment of a DOT scanner for use in a wireless terminal.

FIG. 14A is a perspective assembly view illustration of one embodiment of a DOT scanner 1400 for use in a wireless terminal 14. As illustrated in FIG. 14A, the DOT scanner 1400 comprises a flex circuit 1402 having a CMOS camera attached. A first positioning piece 1404 is coupled to the flex circuit 1402, and a shielding piece 1406 is positioned over the CMOS camera on the flex circuit 1402. A lens 1414 is inserted into a lens sleeve 1410, and a lens retaining ring 1412 is coupled to the lens sleeve 1410 to retain the lens in the lens sleeve 1410. An outer sleeve 1414 is positioned substantially surrounding the lens sleeve 1410 and is configured to focus the CMOS camera, via positioning of the lens within the outer sleeve 1414, such that a central viewing axis of the CMOS camera is perpendicular to a DOT over which the camera is positioned. The outer sleeve 1414 is positioned in a first narrow aperture 1416 of a nose cone 1418, wherein the nose cone 1418 is configured to ensure the CMOS camera is positioned an optimal distance from a DOT during a scanning event. The nose cone 1418 also comprises a second opening 1420 opposite the first narrow aperture 1416. The second opening 1420 has a greater circumference than that of the first narrow aperture 1416 and is configured to be positioned over and encircling a DOT for scanning. The nose cone 1418 further comprises a second narrow aperture 1422 positioned substantially adjacent to the first narrow aperture 1416, and configured to receive an LED 1424 and an LED sleeve 1426. The nose cone 1418 is configured to focus light from the LED 1418 at the second opening 1420 of the nose cone 1418 so as to illuminate a DOT during a DOT scanning event.

Figure 14B:
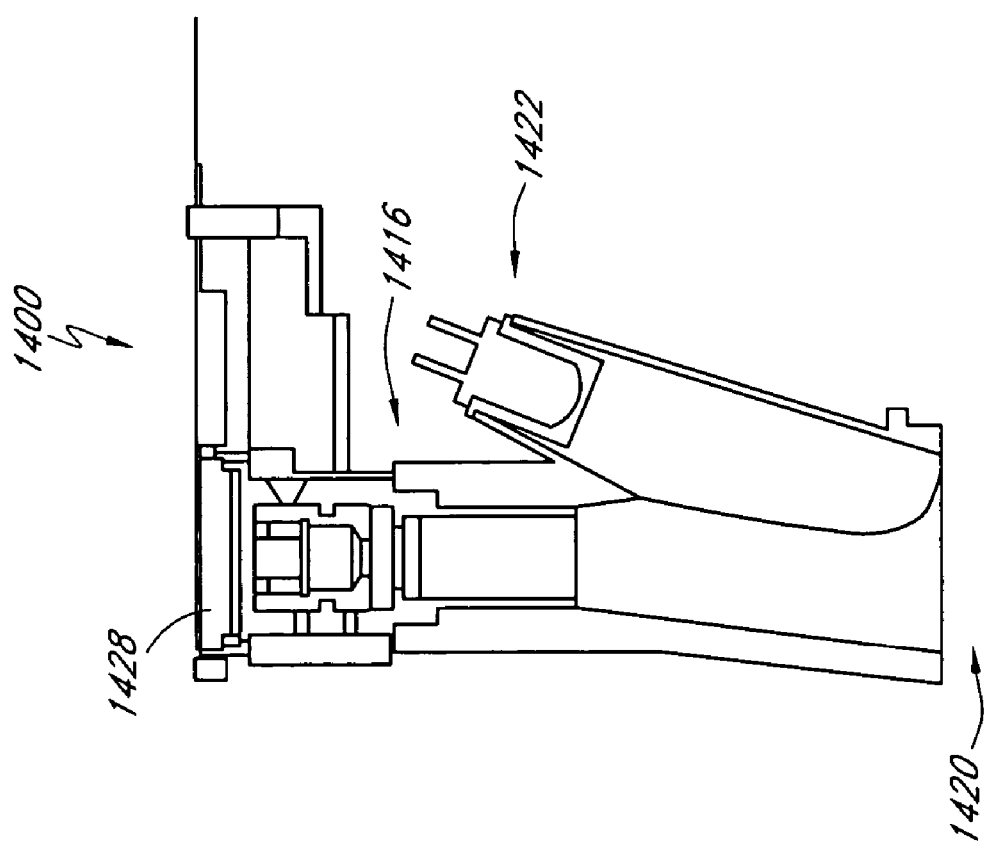
FIG. 14B is a cross-sectional view of the assembled DOT scanner of FIG. 14A.

The assembled scanner 1400 is illustrated in more detail in FIG. 14B, where FIG. 14B is a cross-sectional illustration of the assembled DOT scanner 1400 of FIG. 14A. The configuration of the nose cone 1418 with respect to the fist narrow aperture 1416 and the second narrow aperture 1422 is more clearly illustrated in FIG. 14B, and a CMOS camera 1428 is visible as coupled to the flex circuit 1402. As illustrated in FIG. 14B, the portion of the nose cone 1418 extending from the second narrow aperture 1422 merges with the portion of the nose cone 1418 extending from the first narrow aperture 1416. Thereby, a DOT positioned at the second opening 1420 is illuminated by the LED 1424 positioned at the second narrow aperture 1422, while the CMOS camera 1428 captures an image of the DOT through the first narrow aperture 1416.

Figure 15:
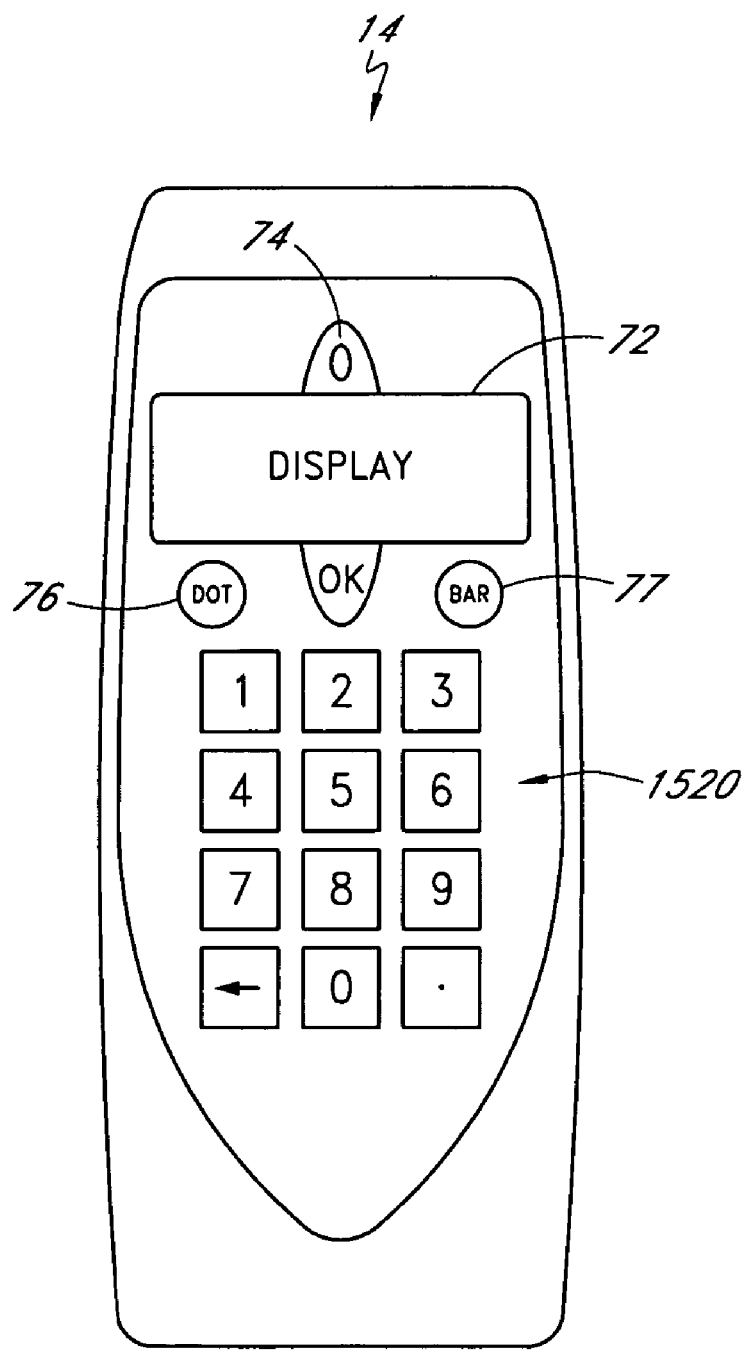
FIG. 15 is an illustration of an additional embodiment of a wireless terminal.

FIG. 15 is a top view illustration of an additional embodiment of a terminal 14. As illustrated in FIG. 15, the terminal 14 includes a numeric keypad 1520 for user input. The numeric keypad 1520 comprises ten numeric keypad buttons corresponding to the numbers zero through nine, a decimal point button, and a backspace button. Alternately, the keypad 1520 may be implemented in a configuration corresponding to that used on a standard computer keyboard. As will be appreciated by those skilled in the art, the keypad 1520 can be implemented with a variety of button combinations, and is not limited to the implementation illustrated and described herein. For example, the keypad 1520 may be implemented with an alphanumeric keypad such as those used with a standard telephone keypad.

It will be appreciated that the above-described system can be implemented in additional environments, such as nursing homes, etc. and is not limited to the health care industry. For example, implementation of the system in industries and environments where precise inventory tracking and workflow management can be advantageous.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in according with the appended claims and any equivalents thereof.

What is claimed is:

1. A system for managing administration of medical care, comprising:
    a handheld terminal, comprising a code scanner and a wireless transmitter, wherein said code scanner is configured to read first scan codes corresponding to instructions to be performed by the system, and wherein said terminal is configured to execute said instructions locally in said handheld terminal; and
    a computer, configured to receive said first scan codes from said handheld terminal and initiate a process in response to said first scan codes.

2. The system of claim 1, wherein said computer is in data communication with at least one peripheral device, and wherein said instructions comprise instructions to be performed by said at least one peripheral device.

3. The system of claim 2, wherein said peripheral device is a printer.

4. The system of claim 2, wherein said peripheral device is a messaging system.

5. The system of claim 1, wherein said terminal is further configured to transmit user information with said first scan codes read by said code reader to said computer.

6. The system of claim 1, wherein said terminal comprises a display for displaying messages to a user.

7. The system of claim 1, wherein said terminal comprises at least one user input device.

8. The system of claim 7, wherein said user input device comprises a button.

9. The system of claim 7, wherein said user input device is an alphanumeric keypad.

10. The system of claim 1, wherein said terminal comprises a plurality of code scanners.

11. The system of claim 1, wherein said code scanner is configured to read two-dimensional machine readable codes.

12. The system of claim 1, wherein said code scanner is configured to read a barcode.

13. The system of claim 1, wherein said code scanner is further configured to read second scan codes corresponding to data.

14. The system of claim 13, wherein said terminal is configured to determine whether said second scan codes read by said code scanner corresponds to data or an instruction.

15. The system of claim 14, wherein a scan code corresponds to a binary number comprising a plurality of bits, and wherein one of said plurality of bits indicates whether said second scan codes corresponds to data or instruction.

16. The system of claim 1, wherein said computer is configured to communicate with at least one peripheral system, and wherein said instructions comprise instructions to be performed by said at least one peripheral system.

17. The system of claim 16, wherein said at least one peripheral system includes at least one of a messaging system, a pharmacy system, a laboratory system, and a patient record system.

18. A system for managing administration of medical care, comprising:
    a handheld terminal, comprising a code scanner and a wireless transmitter, wherein said code scanner is configured to read scan codes;
    a processor in said handheld terminal configured to determine whether a scan code relates to data or an instruction, wherein if said scan code relates to an instruction, said processor determines whether to execute said instruction locally; and
    a computer, configured to receive said scan codes from the wireless transmitter in said handheld terminal and initiate a process if said instruction is not to be run locally.

19. The system of claim 18, wherein said computer is in data communication with at least one peripheral device, and wherein said instructions comprise instructions to be performed by said at least one peripheral device.

20. The system of claim 19, wherein said peripheral device is a printer.

21. The system of claim 19, wherein said peripheral device is a messaging system.

22. The system of claim 18, wherein said terminal is configured to execute said instruction.

23. The system of claim 18, wherein said terminal is further configured to transmit user information with said scan codes read by said code reader to said computer.

24. The system of claim 18, wherein said terminal comprises a display for displaying messages to a user.

25. The system of claim 18, wherein said terminal comprises at least one user input device.

26. The system of claim 25, wherein said user input device comprises a button.

27. The system of claim 25, wherein said user input device is an alphanumeric keypad.

28. The system of claim 18, wherein said terminal comprises a plurality of code scanners.

29. The system of claim 18, wherein said code scanner is configured to read two-dimensional machine readable codes.

30. The system of claim 18, wherein said code scanner is configured to read a barcode.

31. The system of claim 18, wherein said scan codes corresponds to a binary number comprising a plurality of bits, and wherein one of said plurality of bits indicates whether the scan codes corresponds to data or instruction.

32. The system of claim 18, wherein said computer is configured to communicate with at least one peripheral system, and wherein said instructions comprise instructions to be performed by said at least one peripheral system.

33. The system of claim 32, wherein said at least one peripheral system includes at least one of a messaging system, a pharmacy system, a laboratory system, and a patient record system.

* * * * *

UNITED STATES PATENT AND TRADEMARK OFFICE
CERTIFICATE OF CORRECTION

PATENT NO. : 7,607,571 B2  Page 1 of 1
APPLICATION NO. : 10/857701
DATED : October 27, 2009
INVENTOR(S) : Steusloff et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1456 days.

Signed and Sealed this

Twelfth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,607,571 B2 | Page 1 of 1 |
| APPLICATION NO. | : 10/857701 | |
| DATED | : October 27, 2009 | |
| INVENTOR(S) | : Steusloff et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1456 days.

At Column 23, Line 41, change "according" to --accordance--.

At Column 24, Line 18, Claim 14, change "corresponds" to --correspond--.

At Column 24, Line 22, Claim 15, change "corresponds" to --correspond--.

At Column 24, Line 40, Claim 18, change "codes" to --code--.

At Column 24, Line 54, Claim 23, change "codes" to --code--.

At Column 25, Line 3, Claim 31, change "codes" to --code--.

At Column 25, Line 6, Claim 31, change "codes" to --code--.

Signed and Sealed this

Second Day of November, 2010

David J. Kappos
*Director of the United States Patent and Trademark Office*